(12) United States Patent
Kramer et al.

(10) Patent No.: US 12,014,829 B2
(45) Date of Patent: Jun. 18, 2024

(54) IMAGE PROCESSING AND PRESENTATION TECHNIQUES FOR ENHANCED PROCTORING SESSIONS

(71) Applicant: EMED LABS, LLC, Miami, FL (US)

(72) Inventors: Nicholas Atkinson Kramer, Wilton Manors, FL (US); Chistopher T. Larkin, Southwest Ranches, FL (US); Christopher Richard Williams, Miami, FL (US); John Andrew Sands, Weston, FL (US); Colman Thomas Bryant, Fort Lauderdale, FL (US); Glen Crampton McKnight, Vallejo, CA (US); Randall Eugene Hand, Parkland, FL (US)

(73) Assignee: EMED LABS, LLC, Miami, FL (US)

( * ) Notice: Subject to any disclaimer, the term of this patent is extended or adjusted under 35 U.S.C. 154(b) by 106 days.

(21) Appl. No.: 17/661,533

(22) Filed: Apr. 29, 2022

(65) Prior Publication Data
US 2023/0063441 A1    Mar. 2, 2023

Related U.S. Application Data

(60) Provisional application No. 63/362,999, filed on Apr. 14, 2022, provisional application No. 63/268,678, (Continued)

(51) Int. Cl.
*G16H 50/20* (2018.01)
*G06T 5/50* (2006.01)
(Continued)

(52) U.S. Cl.
CPC ............... *G16H 50/20* (2018.01); *G06T 5/50* (2013.01); *G06T 5/92* (2024.01); *G06V 10/25* (2022.01);
(Continued)

(58) Field of Classification Search
CPC ........ G16H 50/20; G16H 40/67; G06V 10/25; G06V 40/172; G06V 10/751; G06V 20/41;
(Continued)

(56) References Cited

U.S. PATENT DOCUMENTS 7,110,525 B1   9/2006   Heller et al.
7,176,936 B2   2/2007   Sauer et al.
(Continued)

FOREIGN PATENT DOCUMENTS

CN   103153248   6/2013
CN   105266897   1/2016
(Continued)

OTHER PUBLICATIONS

Abbott, Dec. 2020, Binaxnow™ covid-19 Ag card home test and Navica™ app, https://web.archive.org/web/20201224151604/https://wwww.globalpointofcare/abbott, 3 pp.
(Continued)

*Primary Examiner* — Jin Ge
(74) *Attorney, Agent, or Firm* — Perkins Coie LLP

(57) ABSTRACT

Systems and methods for providing remotely proctored at-home health testing and diagnostics are provided herein. In particular, systems and methods for improving proctor performance by increasing accuracy and reducing proctor time are disclosed. In some embodiments, images and/or video of a patient may be enhanced to aid the proctor. In some embodiments, proctor performance may be evaluated. In some embodiments, proctor time per patient may be reduced by automating one or more steps in a proctored testing process.

9 Claims, 35 Drawing Sheets

Related U.S. Application Data filed on Feb. 28, 2022, provisional application No. 63/266,139, filed on Dec. 29, 2021, provisional application No. 63/284,482, filed on Nov. 30, 2021, provisional application No. 63/263,220, filed on Oct. 28, 2021, provisional application No. 63/261,710, filed on Sep. 27, 2021, provisional application No. 63/239,792, filed on Sep. 1, 2021.

(51) Int. Cl.
| | |
|---|---|
| *G06T 5/92* | (2024.01) |
| *G06V 10/25* | (2022.01) |
| *G06V 10/75* | (2022.01) |
| *G06V 10/774* | (2022.01) |
| *G06V 20/40* | (2022.01) |
| *G06V 30/41* | (2022.01) |
| *G06V 40/16* | (2022.01) |
| *G16H 40/67* | (2018.01) |
| *H04N 5/272* | (2006.01) |

(52) U.S. Cl.
CPC .......... *G06V 10/751* (2022.01); *G06V 10/774* (2022.01); *G06V 20/41* (2022.01); *G06V 30/41* (2022.01); *G06V 40/172* (2022.01); *G16H 40/67* (2018.01); *H04N 5/272* (2013.01); *G06T 2207/20212* (2013.01)

(58) Field of Classification Search
CPC ...... G06V 30/41; G06V 10/774; G06T 5/009; G06T 5/50; G06T 2207/20212; H04N 5/272
USPC ........................................................ 345/633
See application file for complete search history.

(56) References Cited

U.S. PATENT DOCUMENTS

| | | |
|---|---|---|
| 7,491,198 B2 | 2/2009 | Kockro |
| 7,662,113 B2 | 2/2010 | Pearl et al. |
| 8,108,190 B2 | 8/2012 | Riener et al. |
| 8,253,778 B2 | 11/2012 | Atsushi |
| 8,314,815 B2 | 11/2012 | Navab et al. |
| 8,520,080 B2 | 8/2013 | Havens |
| 8,485,038 B2 | 12/2013 | Sengupta et al. |
| 8,611,988 B2 | 12/2013 | Miyamoto |
| 8,713,130 B2 | 7/2014 | Logan et al. |
| 8,768,022 B2 | 8/2014 | Miga et al. |
| 8,814,691 B2 | 12/2014 | Haddick et al. |
| 8,911,358 B2 | 12/2014 | Koninckx |
| 8,948,935 B1 | 3/2015 | Peeters et al. |
| 8,982,156 B2 | 5/2015 | Maggiore |
| 9,030,446 B2 | 7/2015 | Mistry et al. |
| 9,082,319 B2 | 8/2015 | Shimada et al. |
| 9,111,383 B2 | 8/2015 | Fein et al. |
| 9,256,711 B2 | 2/2016 | Horseman |
| 9,262,743 B2 | 3/2016 | Heins et al. |
| 9,285,871 B2 | 5/2016 | Geisner et al. |
| 9,338,622 B2 | 5/2016 | Bjontegard |
| 9,345,957 B2 | 6/2016 | Geisner et al. |
| 9,380,177 B1 | 8/2016 | Rao et al. |
| 9,424,761 B2 | 11/2016 | Tuchschmid et al. |
| 9,498,132 B2 | 11/2016 | Maier-Hein et al. |
| 9,547,917 B2 | 2/2017 | Zamer |
| 9,563,266 B2 | 3/2017 | Banerjee et al. |
| 9,600,934 B2 | 3/2017 | Odessky et al. |
| 9,606,992 B2 | 5/2017 | Geisner et al. |
| 9,648,436 B2 | 5/2017 | Kraft |
| 9,788,714 B2 | 12/2017 | Krueger |
| 9,836,888 B2 | 12/2017 | Skidmore |
| 9,877,642 B2 | 2/2018 | Duret |
| 9,886,458 B2 | 2/2018 | Jung et al. |
| 9,892,561 B2 | 2/2018 | Choukroun et al. |
| 9,898,662 B2 | 3/2018 | Tsuda et al. |
| 9,916,002 B2 | 5/2018 | Petrovskaya et al. |
| 9,972,137 B2 | 7/2018 | Petrovskaya et al. |
| 10,013,896 B2 | 8/2018 | Feins et al. |
| 10,052,026 B1 | 10/2018 | Tran |
| 10,106,172 B2 | 10/2018 | Wingfield et al. |
| 10,108,266 B2 | 11/2018 | Banerjee et al. |
| 10,127,734 B2 | 12/2018 | Strolla |
| 10,156,900 B2 | 12/2018 | Publicover et al. |
| 10,197,803 B2 | 2/2019 | Badiali et al. |
| 10,216,957 B2 | 3/2019 | Jung et al. |
| 10,244,198 B2 | 3/2019 | Cizerle |
| 10,231,614 B2 | 5/2019 | Krueger |
| 10,295,815 B2 | 6/2019 | Romanowski et al. |
| 10,322,313 B2 | 7/2019 | McKirdy |
| 10,346,889 B1 | 8/2019 | Reiss et al. |
| 10,386,918 B2 | 10/2019 | Shin |
| 10,430,985 B2 | 11/2019 | Harrises et al. |
| 10,474,233 B2 | 11/2019 | Swaminathan et al. |
| 10,524,715 B2 | 1/2020 | Sahin |
| 10,535,202 B2 | 1/2020 | Schmirler et al. |
| 10,540,776 B2 | 2/2020 | Tran et al. |
| 10,559,117 B2 | 3/2020 | Kaeser et al. |
| 10,593,092 B2 | 5/2020 | Solomon |
| 10,643,210 B2 | 5/2020 | Smith et al. |
| 10,660,522 B2 | 5/2020 | Redei |
| 10,664,572 B2 | 9/2020 | Bitran et al. |
| 10,758,209 B2 | 9/2020 | Boctor et al. |
| 10,788,791 B2 | 10/2020 | Gelman et al. |
| 10,802,695 B2 | 11/2020 | Daniels et al. |
| 10,824,310 B2 | 11/2020 | Acharya et al. |
| 10,832,488 B2 | 12/2020 | Petrovskaya et al. |
| 10,849,688 B2 | 12/2020 | Rios et al. |
| 10,885,530 B2 | 1/2021 | Mercury et al. |
| 10,888,389 B2 | 1/2021 | Draelos et al. |
| 10,892,052 B2 | 2/2021 | Jordan et al. |
| 10,910,016 B2 | 3/2021 | Rothschild et al. |
| 10,932,705 B2 | 3/2021 | Muhsin et al. |
| 10,943,407 B1 | 3/2021 | Morgan et al. |
| 10,945,807 B2 | 3/2021 | Gibby et al. |
| 10,957,111 B2 | 4/2021 | Weisman et al. |
| 10,984,910 B2 | 4/2021 | Burkholz et al. |
| 10,991,190 B1 | 4/2021 | Luthra et al. |
| 10,991,461 B2 | 5/2021 | Divine et al. |
| 11,004,271 B2 | 5/2021 | Cvetko et al. |
| 11,017,694 B2 | 10/2021 | Buras et al. |
| 11,152,093 B1 | 10/2021 | Hopen, Sr. et al. |
| 11,194,995 B1 | 12/2021 | Profida Ferreira et al. |
| 11,257,572 B1 | 2/2022 | Narke et al. |
| 11,219,428 B2 | 3/2022 | Burkholz |
| 11,270,235 B1 | 3/2022 | Daianu et al. |
| 11,289,196 B1 | 3/2022 | Ferro, Jr. et al. |
| 11,315,053 B1 | 4/2022 | Powell et al. |
| 11,367,530 B1 | 6/2022 | Ferro, Jr. et al. |
| 11,369,454 B1 | 6/2022 | Ferro, Jr. et al. |
| 11,373,756 B1 | 6/2022 | Ferro, Jr. et al. |
| 11,393,586 B1 | 7/2022 | Ferro, Jr. et al. |
| 2007/0048723 A1 | 3/2007 | Brewer et al. |
| 2009/0004055 A1 | 1/2009 | Darrigrand et al. |
| 2009/0263775 A1 | 10/2009 | Ullrich |
| 2010/0121156 A1 | 5/2010 | Yoo |
| 2010/0159434 A1 | 6/2010 | Lampotang et al. |
| 2011/0164105 A1 | 7/2011 | Lee |
| 2011/0188713 A1* | 8/2011 | Chin .................... G06F 16/583 382/118 |
| 2011/0207108 A1 | 8/2011 | Dorman |
| 2012/0053955 A1 | 3/2012 | Martin et al. |
| 2012/0221960 A1 | 8/2012 | Robinson |
| 2013/0096937 A1 | 4/2013 | Campbell et al. |
| 2013/0253339 A1 | 9/2013 | Reyes |
| 2013/0328997 A1 | 12/2013 | Desai |
| 2013/0344470 A1 | 12/2013 | Morgan et al. |
| 2014/0160264 A1 | 6/2014 | Taylor et al. |
| 2014/0253590 A1 | 9/2014 | Needham et al. |
| 2014/0304335 A1 | 10/2014 | Fung et al. |
| 2015/0187048 A1 | 7/2015 | Johnson |
| 2016/0125765 A1 | 5/2016 | Meretei et al. |
| 2016/0189573 A1 | 6/2016 | Bush |
| 2016/0259911 A1 | 9/2016 | Koester |
| 2016/0292378 A1 | 10/2016 | Saric |

(56) References Cited

U.S. PATENT DOCUMENTS

| | | |
|---|---|---|
| 2016/0371884 A1 | 12/2016 | Benko et al. |
| 2017/0103440 A1 | 4/2017 | Xing et al. |
| 2017/0115742 A1 | 4/2017 | Xing et al. |
| 2017/0146801 A1 | 5/2017 | Stempora |
| 2017/0173262 A1 | 6/2017 | Veltz |
| 2017/0323062 A1 | 11/2017 | Djajadiningrat et al. |
| 2017/0347022 A1* | 11/2017 | Pettersson ............ H04N 23/698 |
| 2018/0012176 A1 | 1/2018 | McHale |
| 2018/0039737 A1 | 2/2018 | Dempers et al. |
| 2018/0092595 A1 | 4/2018 | Chen et al. |
| 2018/0140362 A1 | 5/2018 | Cali et al. |
| 2018/0173913 A1 | 6/2018 | Pulitzer et al. |
| 2018/0197624 A1 | 7/2018 | Robaina et al. |
| 2018/0225982 A1 | 8/2018 | Jaeh et al. |
| 2018/0253840 A1 | 9/2018 | Tran |
| 2018/0341919 A1 | 11/2018 | Luhman |
| 2018/0353073 A1 | 12/2018 | Boucher et al. |
| 2019/0000564 A1 | 1/2019 | Navab et al. |
| 2019/0005195 A1 | 1/2019 | Peterson |
| 2019/0012176 A1 | 1/2019 | McHale |
| 2019/0020651 A1 | 1/2019 | Soon-Shiong et al. |
| 2019/0025919 A1 | 1/2019 | Tadi et al. |
| 2019/0064520 A1 | 2/2019 | Christensen |
| 2019/0073110 A1 | 3/2019 | Bradley et al. |
| 2019/0087951 A1 | 3/2019 | Hanina |
| 2019/0089701 A1* | 3/2019 | Mercury ................ G06F 30/20 |
| 2019/0139318 A1 | 5/2019 | Tierney et al. |
| 2019/0179584 A1 | 6/2019 | Masters |
| 2019/0206134 A1 | 7/2019 | Devam et al. |
| 2019/0216452 A1 | 8/2019 | Nawana et al. |
| 2019/0259483 A1 | 8/2019 | Potts |
| 2019/0261914 A1 | 8/2019 | Davis et al. |
| 2019/0341152 A1* | 11/2019 | Mellem ................ G16H 50/30 |
| 2019/0346429 A1 | 11/2019 | Harris |
| 2019/0266663 A1 | 12/2019 | Keeler et al. |
| 2019/0378080 A1 | 12/2019 | Srinivasan et al. |
| 2019/0380790 A1 | 12/2019 | Fuchs et al. |
| 2019/0391638 A1 | 12/2019 | Khaderi et al. |
| 2020/0000401 A1 | 1/2020 | Dullen |
| 2020/0020454 A1 | 1/2020 | McGarvey |
| 2020/0020171 A1 | 3/2020 | Hendricks et al. |
| 2020/0073143 A1 | 4/2020 | Macnamara et al. |
| 2020/0101367 A1 | 5/2020 | Tran et al. |
| 2020/0152339 A1 | 6/2020 | Pulitzer et al. |
| 2020/0174756 A1 | 6/2020 | Cerar et al. |
| 2020/0175769 A1 | 7/2020 | Mandala |
| 2020/0205913 A1 | 7/2020 | Carnes et al. |
| 2020/0207501 A1 | 7/2020 | Urquhart et al. |
| 2020/0211291 A1 | 7/2020 | Miller et al. |
| 2020/0226758 A1 | 8/2020 | Carnes et al. |
| 2020/0250389 A1 | 9/2020 | Pulitzer et al. |
| 2020/0303044 A1 | 10/2020 | Stephen |
| 2020/0312038 A1 | 10/2020 | Samec et al. |
| 2020/0312437 A1 | 10/2020 | Wendland |
| 2020/0337631 A1 | 10/2020 | Sahin |
| 2020/0342679 A1 | 12/2020 | Soon-Shiong |
| 2020/0405257 A1 | 12/2020 | Samec et al. |
| 2020/0409159 A1 | 12/2020 | Samec et al. |
| 2021/0015583 A1 | 1/2021 | Avisar |
| 2021/0022810 A1 | 2/2021 | Mahfouz |
| 2021/0058485 A1 | 3/2021 | Devam et al. |
| 2021/0082554 A1 | 3/2021 | Kalia |
| 2021/0086989 A1 | 4/2021 | Luxford |
| 2021/0118029 A1 | 4/2021 | Koritala |
| 2021/0183507 A1 | 6/2021 | Shaya |
| 2021/0326474 A1 | 10/2021 | Sparks et al. |
| 2021/0327304 A1 | 11/2021 | Buras |
| 2021/0350883 A1 | 11/2021 | Li et al. |
| 2021/0358068 A1 | 11/2021 | Boszczyk et al. |
| 2022/0020236 A1 | 1/2022 | Luthra et al. |
| 2022/0074000 A1 | 3/2022 | Wong |
| 2022/0101608 A1 | 3/2022 | Hu |
| 2022/0223281 A1 | 7/2022 | Ferro |
| 2022/0223282 A1 | 7/2022 | Ferro |
| 2022/0223300 A1 | 7/2022 | Ferro |

FOREIGN PATENT DOCUMENTS

| | | |
|---|---|---|
| EP | 3 872 813 | 9/2021 |
| KR | 10-2008-0012745 | 2/2008 |
| KR | 10-2018-0068703 | 6/2018 |
| WO | WO 21/044064 | 3/2021 |
| WO | WO 21/171226 | 9/2021 |

OTHER PUBLICATIONS

Baruah, Basant, "Augmented reality and QR codes—What you need to know", accessed via wayback machine for Apr. 14, 2021, beaconstac blog.

Uber expands options for prescription delivery with ScriptDrop, Mar. 24, 2021, Uber.com Blog (Year: 2021).

Zheng, Lixia, "Using Augmented Reality with Interactive Narrative to Help Paediatric Patients Take Prescription Medication", 2020, University College London.

* cited by examiner

IMAGE PROCESSING AND PRESENTATION TECHNIQUES FOR ENHANCED PROCTORING SESSIONS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit under 35 U.S.C. § 119(e) to U.S. Provisional Patent Application No. 63/239,792, filed Sep. 1, 2021, entitled "IMAGE PROCESSING AND PRESENTATION TECHNIQUES FOR ENHANCED PROCTORING SESSIONS," U.S. Provisional Patent Application No. 63/261,710, filed Sep. 27, 2021, entitled "IMAGE PROCESSING AND PRESENTATION TECHNIQUES FOR ENHANCED PROCTORING SESSIONS," U.S. Provisional Patent Application No. 63/263,220, filed Oct. 28, 2021, entitled "IMAGE PROCESSING AND PRESENTATION TECHNIQUES FOR ENHANCED PROCTORING SESSIONS," U.S. Provisional Patent Application No. 63/266,139, filed Dec. 29, 2021, entitled "IMAGE PROCESSING AND PRESENTATION TECHNIQUES FOR ENHANCED PROCTORING SESSIONS," U.S. Provisional Patent Application No. 63/268,678, filed Feb. 28, 2022, entitled "IMAGE PROCESSING AND PRESENTATION TECHNIQUES FOR ENHANCED PROCTORING SESSIONS," U.S. Provisional Patent Application No. 63/284,482, filed Nov. 30, 2021, entitled "PROCTOR TIME REDUCTION TECHNIQUES," and U.S. Provisional Patent Application No. 63/362,999, filed Apr. 14, 2022, entitled "AUGMENTED REALITY DIAGNOSTIC TEST PREFLIGHT SETUP." The entirety of all of these applications is incorporated by reference herein.

BACKGROUND

Field

The present application is directed to remote medical diagnostic testing. This application relates to proctored testing sessions, and more particularly, to image processing and presentation techniques for enhanced proctored testing sessions. In some embodiments, the devices, systems, and methods for image processing and presentation techniques for enhanced proctoring sessions described herein can be included in or used in conjunction with computerized testing. Some embodiments are directed to methods, systems, and devices for reducing proctor time during a proctored testing session.

Description

The use of telehealth to deliver health care services has grown consistently over the last several decades and has experienced very rapid growth in the last several years. Telehealth can include the distribution of health-related services and information via electronic information and telecommunication technologies. Telehealth can allow for long-distance patient and health provider contact, care, advice, reminders, education, intervention, monitoring, and remote admissions. Often, telehealth can involve the use of a user or patient's personal device, such as a smartphone, tablet, laptop, personal computer, or other type of personal device. For example, the user or patient can interact with a remotely located medical care provider using live video and/or audio through the personal device.

Remote or at-home health care testing and diagnostics can solve or alleviate some problems associated with in-person testing. For example, health insurance may not be required, travel to a testing site is avoided, and tests can be completed at a patient's convenience. However, at-home testing introduces various additional logistical and technical issues, such as guaranteeing timely test delivery to a patient's home, providing test delivery from a patient to an appropriate lab, ensuring test verification and integrity, providing test result reporting to appropriate authorities and medical providers, and connecting patients with medical providers, who are needed to provide guidance and/or oversight of the testing procedures remotely.

SUMMARY

While remote or at-home health care testing offers many benefits, there are several difficulties. For example, the time required for each proctor to administer a proctored testing session may be lengthy, leading to patient wait times and/or increased cost as more proctors may be needed to facilitate patient throughput. Poor image quality or failure to capture needed images and information may cause further delays as users are given further instructions and steps of tests and/or entire tests need to be repeated.

This application describes systems, methods, and devices for reducing proctor time during proctored testing sessions. These systems, methods, and devices may decrease the total time a proctor must spend on a proctored testing session, which may, for example, allow the proctor to provide more proctored sessions to more patients. In some embodiments, decreasing proctor time during a proctored testing session may include improving proctor efficiency during proctored portions of a testing session and/or providing non-proctored portions during the testing session that do not require a proctor.

During a proctored testing session, such as an on demand proctored testing session in which a test user is remotely connected by video and/or audio communication over a network to a proctor, the test user can be prompted to present one or more items to the camera. The items can be presented for review by the proctor (which can be a live proctor or an artificial intelligence (AI)-based proctor) and/or so that a view of the items can be recorded (for example, for a later review). These items can include identification, for example, credentials (ID), testing materials, and/or test results, among others. In some instances, however, the proctor's ability to accurately analyze and/or review such items may be hindered by the filming conditions or image quality.

Accordingly, in some instances, an image of such items captured by the camera may need to be enhanced to allow the proctor to effectively analyze such items. Such enhancement can be achieved, in some embodiments, according to the systems, methods, and devices described herein. For example, the devices, systems, and methods described herein may be configured to prompt the test user to present at least one item to the camera at any point during an on-demand proctored testing session, identify the item within an image captured by the camera, and enhance or provide an alternative view of the item. In some embodiments, images of the test user's presentation can be enhanced and displayed in a proctor assist interface. A system may identify a region of interest within the test user's presentation of information and selectively apply a process to enhance the image in a manner that would assist the proctor in accurately analyzing the information provided by the test user.

The image processing and presentation techniques for enhanced proctoring sessions can provide for the following advantages in some embodiments. The techniques can allow a proctor to get a clearer image of a test item or other item, thereby facilitating review and providing a more accurate way to interpret results. Additionally or alternatively, the techniques can expand the range of operation of the camera on the user device, allowing for lower-end or older camera components to be used without issue. This can be beneficial in areas where more advanced technology is not available, such as remote areas, developing countries, or areas of other humanitarian efforts. In some examples, the techniques described herein can enable a forward-facing camera on a smartphone (which is typically lower in quality than the rearward-facing camera) to be utilized for some or all portions of a testing procedure. Further, the techniques can enable an AI to utilize better and cleaner training data (and runtime data).

In one aspect a computer-implemented method for a remote diagnostic testing platform, is disclosed, the computer-implemented method comprising: receiving, by a computing system, a video feed from a user device of a user engaging in an on-demand test session; analyzing, by the computing system, the video feed to automatically determine that a particular step in the on-demand test session has been reached by the user; based on detection of the particular step, storing, by the computing system, a plurality of subsequently-received image frames of the video feed to a first buffer; evaluating, by the computing system, the plurality of image frames stored in the first buffer against a set of criteria; selecting, by the computing system, a subset of the image frames stored in the first buffer based at least in part on the evaluation; storing, by the computing system, the selected subset of image frames to a second buffer; processing, by the computing system, the subset of image frames stored in the second buffer to generate a composite image; and performing, by the computing system, one or more operations using the composite image.

The computer-implemented method can include one or more of the following features in any combination: detecting, by the computing system, that the particular step in the on-demand test session has ended; wherein performing comprises presenting the composite image to a proctor; wherein performing comprises creating or modifying a training data set, the training data set to be used for training a machine learning model; wherein performing comprises extracting, by the computing system, information from the composite image, and querying, by the computing system, a database using the extracted information; wherein processing comprises extracting, by the computing system, a region of interest from each image frame stored in the second buffer, using, by the computing system, template-matching to overlay image data extracted from the frames stored in the second buffer, processing, by the computing system, the overlaid image data to enhance the image, and combining, by the computing system, the processed overlaid image data to form a composite image; wherein enhancing the image comprises any combination of one or more of suppressing noise, normalizing illumination, rejecting motion blur, enhancing resolution, rotating, keystone correcting, or increasing image size; wherein normalizing illumination comprises determining, by the computing system, a size of the region of interest in at least one dimension, accessing, by the computing system, a kernel for normalizing illumination levels in images, dynamically adjusting, by the computing system, a size of the kernel in at least one dimension based at least in part on the determined size of the region of interest, and applying, by the computing system, the adjusted kernel to one or more patches of the region of interest to normalize one or more levels of illumination within the region of interest; providing, to a proctor computing device, the composite image; and/or other features as described herein.

In another aspect, a computer-implemented method for a proctored examination platform is disclosed. The computer-implemented method comprising an identity verification step, wherein the identity verification step comprises: presenting, by a computing system to a user, a request for the user to capture an image of an identification document of the user; presenting, by the computing system to the user, a request for the user to capture an image of a face of the user; receiving, by the computing system from the user, the image of the identification document and the image of the face of the user; extracting, by the computing system, one or more pieces of information from the image of the identification document; and converting, by the computing system, at least one of the one or more pieces of information to a standardized format.

The computer-implemented method can further include one or more of the following features in any combination: displaying, by the computing system to a proctor, the standardized information; requesting, by the computing system, that the proctor verify the standardized information; receiving, by the computing system from the proctor, an indication that the standardized information has been verified by the proctor; comparing, by the computing system, the standardized information to reference information about the user; determining, by the computing system, if the standardized information matches the reference information; and if the standardized information does not match the reference information or if the computing system could not determine if the standardized information matches the reference information: displaying, to a proctor, an indication that the standardized information does not match the reference information or could that the system could not determine if the standardized information matches the reference information; requesting, by the computing system, that the proctor verify the standardized information; receiving, by the computing system from the proctor, an indication that the standardized information has been verified by the proctor; and if the standardized information matches the reference information: displaying, to the proctor, an indication that the standardized information matches the reference information; wherein the reference information comprises user registration information; wherein the reference information comprises information from an external data source, wherein the external data source does not contain user registration information; and/or other features as described herein.

In another aspect, a computer-implemented method for a proctored examination platform is disclosed. The computer-implemented method comprising a test setup verification step, wherein the test setup verification step comprises: detecting, by a computing system, a type of device that a user is using to take a test; displaying, by the computing system to the user, an example test setup, wherein the example test setup is based at least in part on the type of device; and displaying, by the computing system to the user, a view of a camera of the user's device, wherein the view includes one or more overlays indicative of where objects should be positioned.

The computer-implemented method can include one or more of the following features in any combination: wherein detecting the type of device comprises determining one or more of an operating system, a web browser, an application, a user agent, a screen resolution, or a pixel density; and/or other features as described herein.

In another aspect, a computer-implemented method for a proctored examination platform can include: receiving, by a computing system from a user device, a video feed of an on-demand testing session; detecting, by the computing system, that a particular step in the on-demand test session has been reached by the user; measuring, by the computing system, a quality of the video feed; detecting, by the computing system, that the quality of the video feed is below a threshold level; detecting, by the computing system, an object of interest in the video feed; extracting, by the computing system, a region containing the object of interest from the video feed; applying, by the computing system, one or more image transformations to the extracted video region; providing, by the computing system to a proctor device, a video feed transformed extracted video region; and detecting, by the computing system, that an end of the of particular step in the on-demand testing session has been reached by the user.

The computer-implemented method can include one or more of the following features in any combination: wherein the one or more image transformations comprise any combination of one or more of white balancing, denoising, and image stabilization; wherein measuring the quality of the video feed comprises measuring any combination of one or more of blur, compression artifacts, and time since last frame; wherein detecting the object of interest comprises feature matching, and wherein feature matching comprises finding a correspondence between a contents of the frame and a template of the object of interest; wherein extracting the region of interest comprises performing a homographic transformation; and/or other features as described herein.

In another aspect, a computer-implemented method for a proctored examination platform can include: receiving, by a computing system from a user device, a video feed of an on-demand testing session; detecting, by the computing system, information indicative of a quality of the video feed; calculating, by the computing system, one or more assurance levels associated with a testing session; and presenting, by the computing system to a proctor, an indication of the one or more assurance levels.

The computer-implemented method can also include one or more of the following features in any combination: providing, by the computing system to the proctor, one or more recommendations for increasing at least one assurance level of the one or more assurance levels; wherein determining an assurance level comprises determining a lighting quality of the video feed; wherein determining an assurance level comprises determining an image quality of the video feed; wherein determining an image quality comprises determining any combination of one or more of an amount of pixelation, a frame rate, a rate of dropped frames, and a resolution of the video feed; wherein determining an assurance level comprises determining a distance quality of the video feed, wherein the distance quality depends at least in part on a size of an object of interest with respect to a size of a camera viewing area; wherein determining an assurance level comprises determining a distance quality of the video feed, wherein the distance quality depends at least in part on a distance of an object of interest from a camera; determining, by the computing system, an aggregate assurance level based on the one or more assurance levels, and presenting, by the computing system to a proctor, the aggregate assurance level; determining, by the computing system, a test result for the testing session, receiving, by the computing system from the proctor, a test result for the testing session, calculating, by the computing system, an assurance level based at least in part on the determined test result and the received test result; determining, by the computing system, than an assurance level is below a threshold level, and presenting, by the computing system to the proctor, an alert indicating that the assurance level is below the threshold level; and/or other features as described herein.

In another aspect, a computer-implemented method for remote medical testing can include: providing, by a computing system, a web page to a user; determining, by the computing system, if a user device of the user is capable of presenting augmented reality content to the user; and if the user device is capable of presenting augmented reality content, providing, by the computing system, an augmented reality tutorial to the user of the user device; and if the user device is not capable of presenting augmented reality content, providing, by the computing system, a video tutorial to the user of the user device.

The computer-implemented method can include one or more of the following features in any combination: wherein providing the augmented reality tutorial comprises capturing, by the computing system, a video feed of an environment of the user, determining, by the computing system, a testing area in the environment of the use, and displaying, by the computing system, one or more virtual objects on top of the video feed; wherein providing the augmented reality tutorial further comprises receiving, by the computing system, a video feed of the user, determining, by the computing system, one or more facial features of the user, and displaying, by the computing system, at least one virtual object on top of the video feed of the user, wherein a placement of the at least one virtual object is determined at least in part by the one or more determined facial features of the user; and/or other feature as described herein.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present application are described with reference to drawings of certain embodiments, which are intended to illustrate, but not to limit, the present disclosure. It is to be understood that the attached drawings are for the purpose of illustrating concepts disclosed in the present application and may not be to scale.

DETAILED DESCRIPTION

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

As mentioned briefly above and as will now be explained in more detail below with reference to the example embodiments provided in the figures, this application describes devices, systems, and methods for image processing and presentation techniques to enhance proctored sessions. Various embodiments described herein relate to systems, methods, and devices for image processing and presentation techniques for computerized proctored testing sessions. In some instances, the testing user is prompted to present at least one item to the camera. These items can include identification credentials, testing materials, and test results, among others.

Filming conditions and image quality can affect the proctor's ability to accurately analyze such items. Accordingly, it may be beneficial to provide enhancement of the image, for example, to facilitate proctor review of such items. If the filming condition or image quality is not adequate, the proctor may not be able to accurately or effectively analyze the information provided. By dynamically and selectively enhancing the image, the proctor can be assisted in ensuring adequate images of the information provided by the testing user are received. In some embodiments, the image enhancement techniques described herein may be used to improve computer-based recognition, such as extracting information from an identification document, extracting test results, evaluating test setup, and so forth using computer vision systems.

Figure 1:
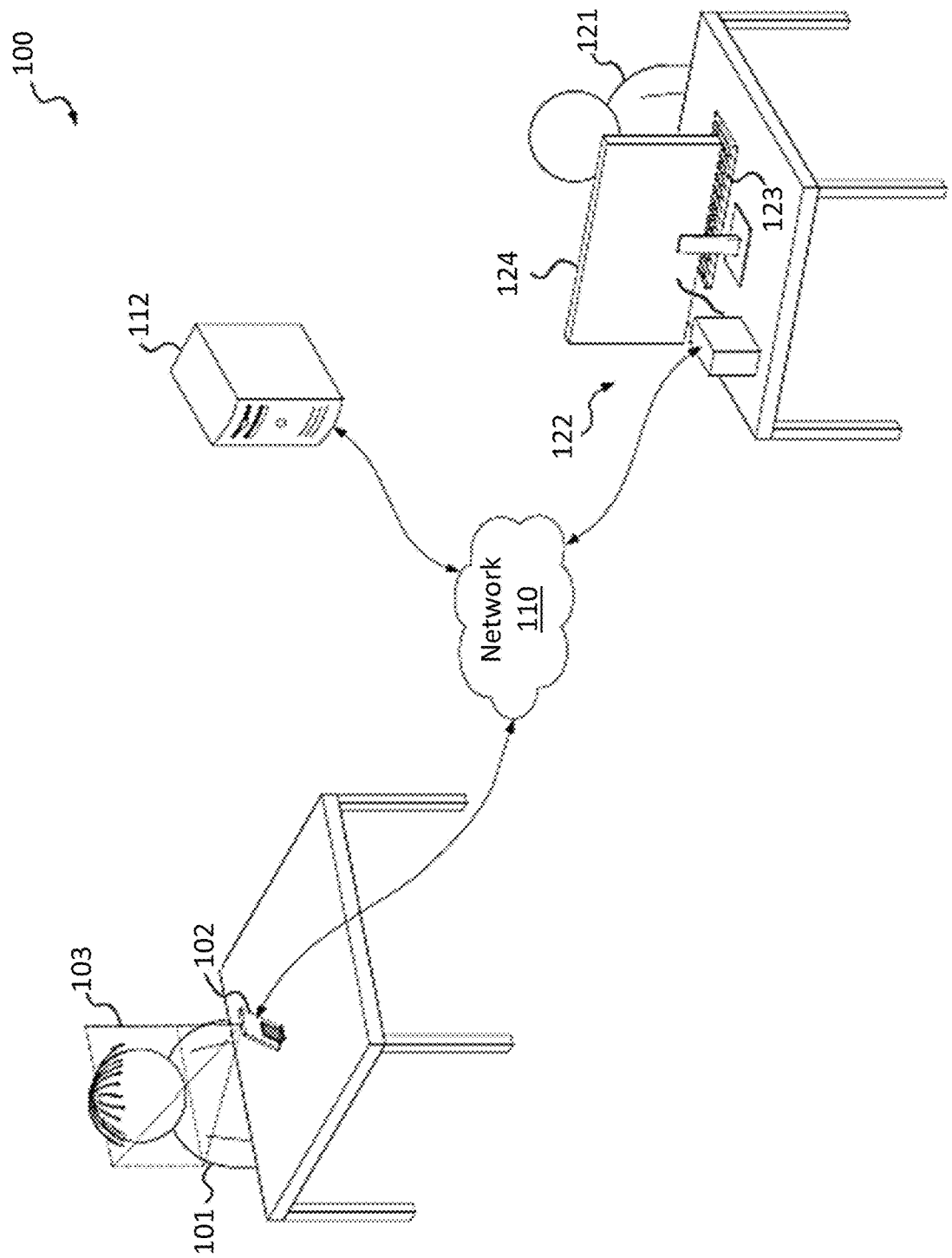
FIG. 1 is a schematic diagram illustrating a proctored test system with a test user, proctor, testing platform, user device, network, and proctor computing device.

FIG. 1 illustrates an arrangement 100 including a test user 101 using a user device 102. The user device 102 includes a camera having field of view 103. In the illustrated embodiment, the user device 102 is a smartphone. In some embodiments, the user device 102 may be a tablet, laptop, or desktop computer, etc.

To facilitate proctoring, the user device 102, a testing platform 112, and a proctor computing device 122 can be communicatively coupled to at least one network 110. The testing platform 112 can allow for the test to be administered. In some embodiments, a proctor 121 can monitor the proctor computing device 122. The proctor computing device 122, may include at least one input device 123 and at least one output device 124. The input device 123 may include a keyboard, mouse, and/or other input computer accessories. The output device 124 may include a display, a speaker, and/or other output computer accessories.

Figure 2:
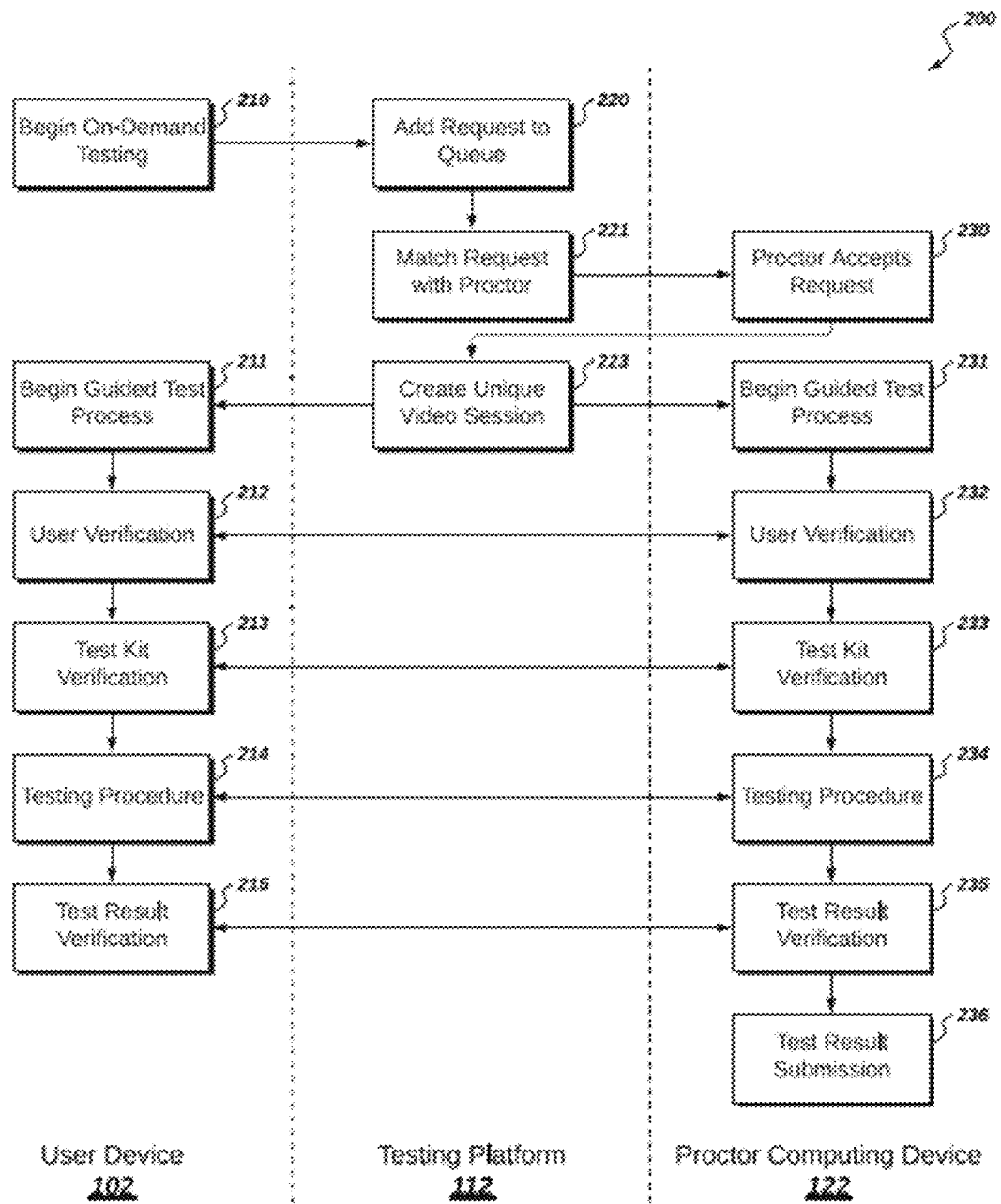
FIG. 2 is a block diagram depicting an on-demand testing protocol with a proctor.

FIG. 2 provides an example of a flowchart of an on-demand testing protocol 200 that may require the proctor 121. The protocol 200 will now be explained with reference to FIG. 2 and continued reference to FIG. 1. In some embodiments, the test user 101 may activate a test kit which can allow the test user 101 to access the testing platform 112 within the network 110 using the user device 102. The user device 102 may allow the testing user 101 to initiate an on-demand testing session at block 210. In some embodiments, the test user's 101 ability to access or activate the on-demand testing session may expire if the time elapsed exceeds a predetermined allotted amount of time.

In some embodiments, the initiation of the on-demand testing session at block 210 may allow the testing platform 112 to place the test user 101 in a virtual waiting room. At block 220, the protocol 200 can include a request to queue, in which the user will be added to a queue of users awaiting an on-demand testing session. As illustrated at block 221, the request to queue 220 can be satisfied upon matching the user 101 with a proctor 121, for example, an available medical provider proctor. At block 230, upon matching, the proctor 121 may select an acceptance of test user's request to begin testing. In some embodiments, the acceptance of the test user's request to begin may, at block 223, initiate a unique one-way or two-way video session between the test user 101 and the proctor 121 provided by the testing platform 112. The video session may, as illustrated at block 211, involve (1) a first guided test process for the test user 101 on the user device 102 (e.g., the user experience), and (2), as illustrated at block 231, a second guided test process 231 for the proctor 121 using the proctor computing device 122 (e.g., the proctor experience).

The proctor 121 and the test user 101 may follow provided instructions through the on-demand testing session appearing on the user device 102 and proctor computing device 122 to, for example, at blocks 212, 232, verify the test user 101. For example, the test user 101 may be prompted to present an identification credential for user verification to the user device 102 for the proctor 121 to review on the proctor computing device 122. In some embodiments, the proctor 121 may compare the identification credentials for user verification with a database of pre-existing images of the test user's identification credentials associated with the test user 101.

The proctor 121 and the test user 101 may follow provided instructions through the on-demand testing session appearing on the respective user device 102 and the proctor computing device 122 to, at blocks 213, 233, verify the test kit. For example, for the test user's test kit verification, the test user may be prompted to present a unique ID printed on or otherwise included in the test kit to the camera 103 for scanning and analysis. In some embodiments, the unique ID can include a string of characters, QR code, graphic, RFID/NFC tag, etc.

In some embodiments, after test kit verification occurring at blocks 213, 233, the proctor 121 may guide the test user 101 through the testing procedure, as illustrated at blocks 214, 234. This may include having the user perform one or more steps of a testing procedure under the supervision of the proctor. As illustrated at blocks 215, 235, upon completion of the test, a test result verification can occur. For example, the user 101 can show the proctor the results of the test (e.g., a test strip), which can be verified by the proctor 121. The proctor 121 may, at block 236, submit and store the verified test results, for example, within a database on the testing platform 112.

Image Processing and Presentation Techniques

Figure 3:
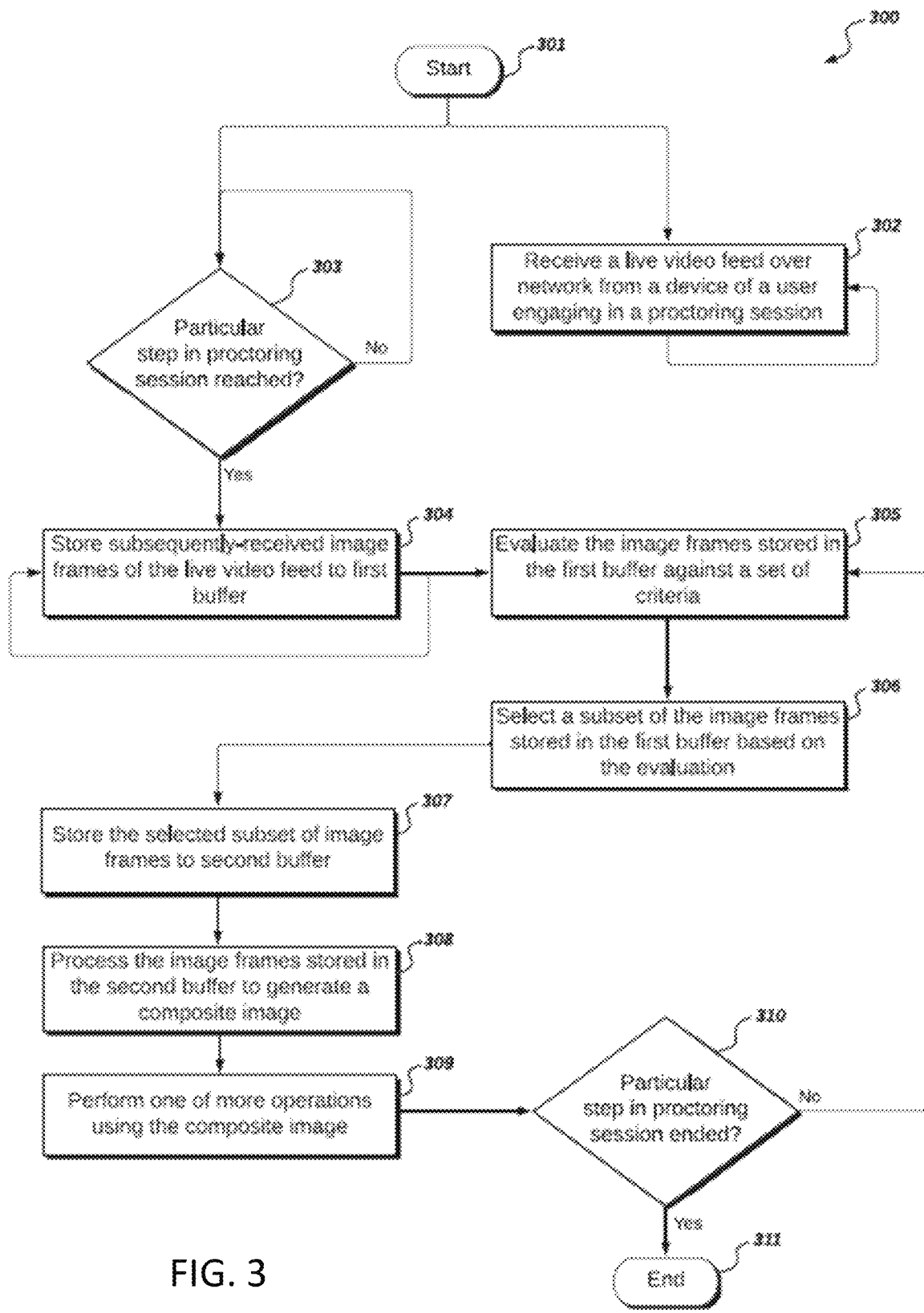
FIG. 3 is a block diagram illustrating an embodiment of a method for the enhancement of proctoring sessions by employing image processing and presentation techniques.
Figure 33:
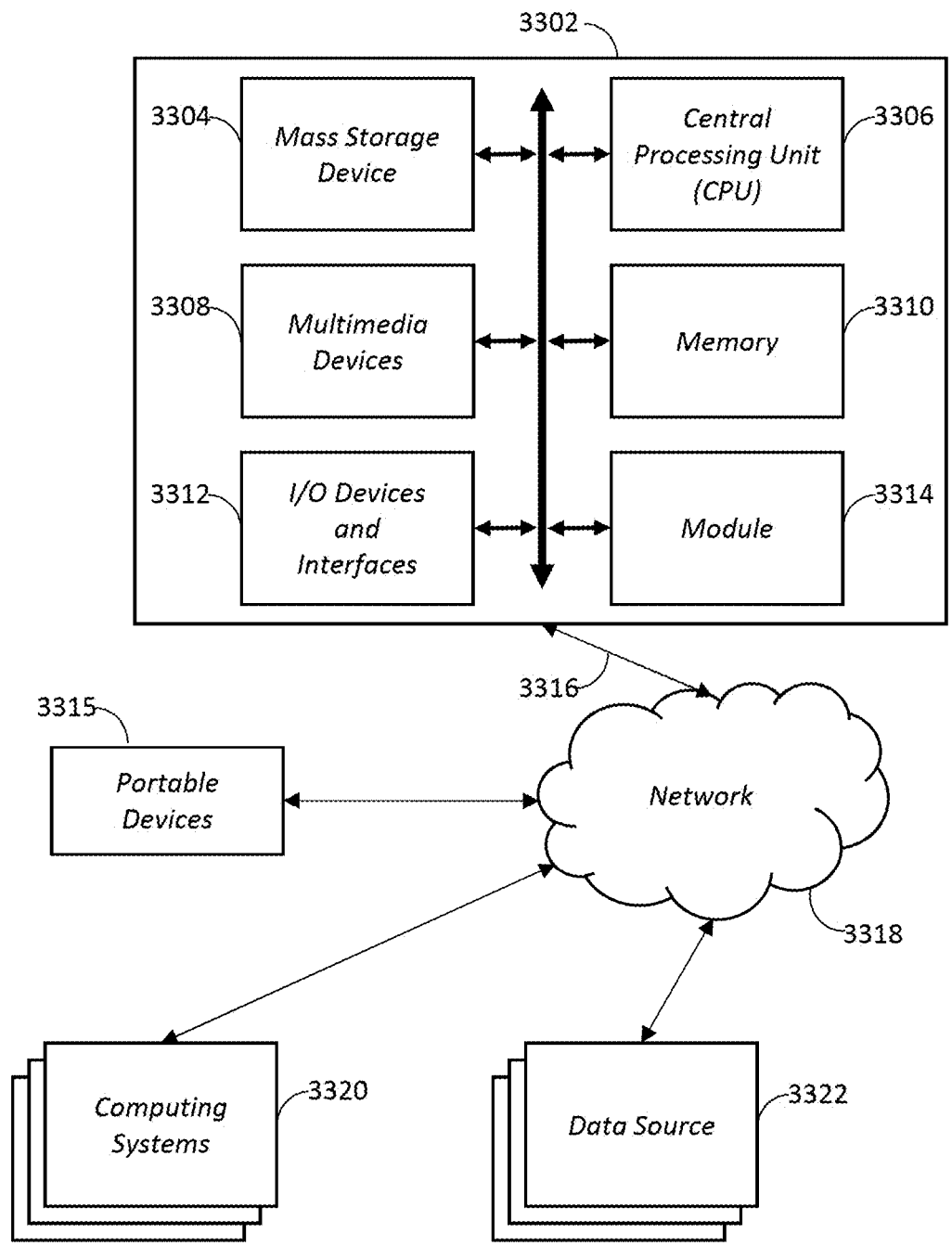
FIG. 33 is a block diagram illustrating an example embodiment of a computer system configured to run software for implementing one or more embodiments of the image processing and presentation techniques for enhanced proctoring session systems, methods, and devices disclosed herein.

FIG. 3 is a flowchart illustrating an overview of an example embodiment of a method 300 for enhancing proctoring sessions by selectively employing image processing and presentation techniques. In some embodiments, the method 300 includes at least one computing device that can be similar to the user device 102, the testing platform 112, or the proctor computing device 122 or other components of a computing system as shown in FIG. 33. In some embodiments, at least one step of the method 300 may be performed in parallel with at least one step of the on-demand testing protocol 200.

The method 300 may begin at block 301. At 302, a live video feed can be received, for example, over the network 110 from the user device 102 engaging in the on-demand test session. In some embodiments, the live video feed 302 may remain throughout the execution of the method 300. In some embodiments, the live video feed 302 may remain even after the method 300 reaches a termination 311.

At block 303, the method 300 can determine whether a particular step in proctoring session has been reached. In some embodiments, such particular step may correspond to at least one step of the on-demand testing protocol 200 of FIG. 2. For example, the method 300 may determine whether user verification (e.g., blocks 212, 232) is satisfied, test kit verification (e.g., blocks 213, 233) is satisfied, and/or test result verification (e.g., blocks 215, 235) is satisfied. In some embodiments, the method 300 may remain in a holding pattern until the particular step in the proctoring session is reached.

Once the particular step in the proctoring session is reached, the method 300 may, at block 304, store subsequently-received image frames of the live video feed to a first buffer. For example, such first buffer may be capable of holding a certain number, m, of image frames. In some embodiments, the first buffer may correspond to a First In, First Out (FIFO) buffer configured to store the m most recent image frames. The method 300 may continuously store subsequently-received image frames of the live video feed to the first buffer throughout the execution of the method 300. The method 300 may, at block 305, evaluate the image frames stored in the first buffer against a set of criteria. The method 300 may, at block 306, select a subset of the image frames stored in the first buffer based on the evaluation of the image frames. For example, the evaluation may involve at least one measure of motion blur, at least one measure of the extent to which the image frame differs from at least one adjacent image frame in the sequence of image frames stored in the first buffer 304, and/or at least one measure of camera exposure, among others.

In some embodiments, the method 300 may rank the image frames stored in the first buffer based on the evaluation. For example, images that exhibit relatively low amounts of motion blur, differ from at least one adjacent image frame to a relatively great extent, and exhibit camera exposure levels that are closer in value to a predetermined exposure level may be favored by the method 300. The method 300 may, at block 307, store the subset of image frames selected at block 306 to a second buffer. For example, such second buffer may be capable of holding a certain number, n, image frames, where n<m. In some embodiments, the second buffer may involve overwriting at least one image frame already stored in the second buffer with at least one image frame selected at block 306, or a combination thereof. The images stored in the second buffer may then, at block 308, be processed to generate a composite image. The method 300 may then, at block 309, selectively perform at least one operation using the composite image. For example, such operation may involve providing the composite image for presentation through a proctor assist tools interface, using the composite image to query at least one database, storing the composite image and/or at least one additional data point generated on the basis thereof, and/or using the composite image to train at least one machine learning model.

The method 300 may, at block 310, determine whether the particular step in the proctoring session has concluded. In some embodiments, if the particular step in the proctoring session has not concluded, the method 300 may continue by repeating the process described above until the particular step in the proctoring session has concluded. In some embodiments, if the particular step in the proctoring session has concluded, the method 300 can terminate at block 311.

Example Enhancing Techniques

Figure 4:
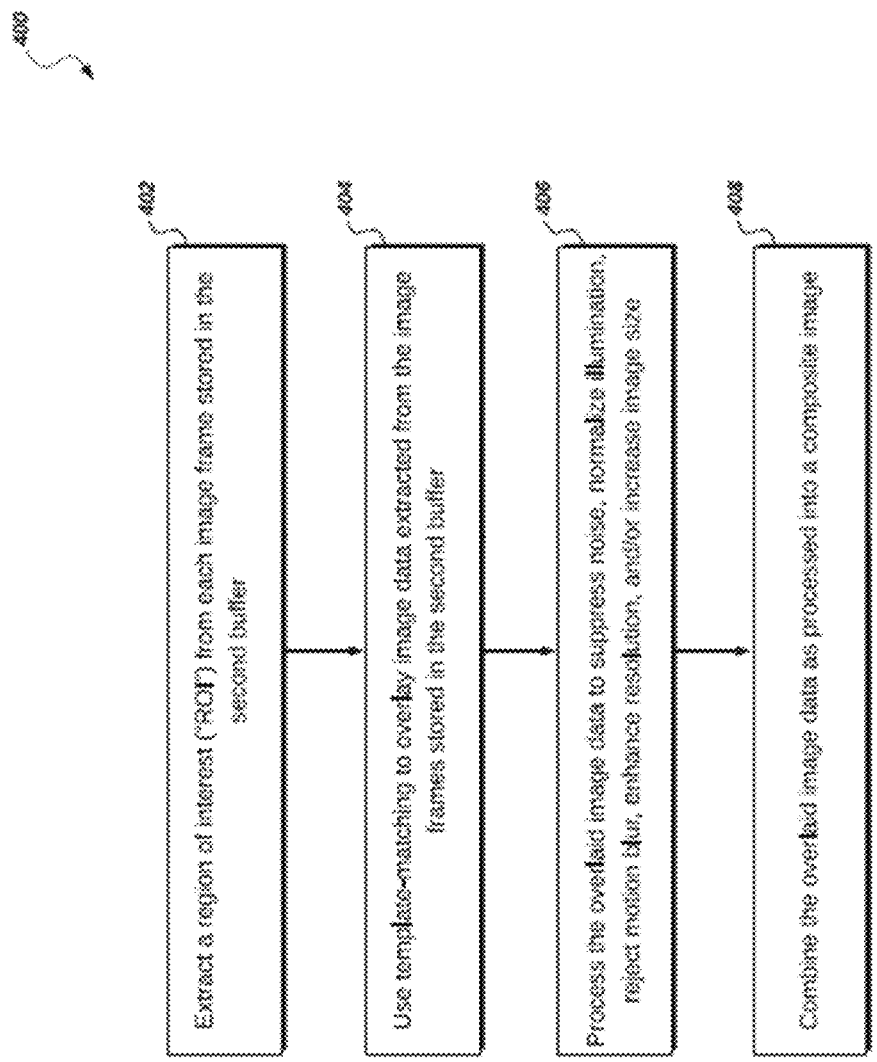
FIG. 4 is a block diagram illustrating an embodiment of a method for the processing of image frames to generate composite images for enhancing proctoring sessions.

FIG. 4 is a flowchart illustrating an overview of an embodiment of a method 400 for processing and enhancing image frames to generate composite images. For example, the method 400 may be implemented using at least one computing device that is similar or equivalent to the user device 102, the testing platform 112, the proctor computing device 122, and/or other suitable computing device. The method 400 may, in some embodiments, represent or be used during blocks of the method 300.

In some embodiments, the method 400 can be, at block 402, configured to selectively extract at least one region of interest from one or more image frames stored in the second buffer (e.g., at block 307 of FIG. 3). At block 404, the method 400 may be configured to use template-matching to overlay the image data extracted from the image frames stored in the second buffer. The method 400 may also, as illustrated at block 406, be configured to selectively process the overlaid image data to improve the image. For example, the improvements may include suppressing noise, normalizing illumination, rejecting motion blur, enhancing resolution, rotating, de-skewing, keystone correction, and/or increasing image size, among others. The method 400 can, at block 408, combine the overlaid image data as processed into a composite image. In some embodiments where more than one region of interest is extracted (e.g., at block 402), the method 400, may perform blocks 404, 406, and 408 for each extracted region of interest.

Figure 5A:
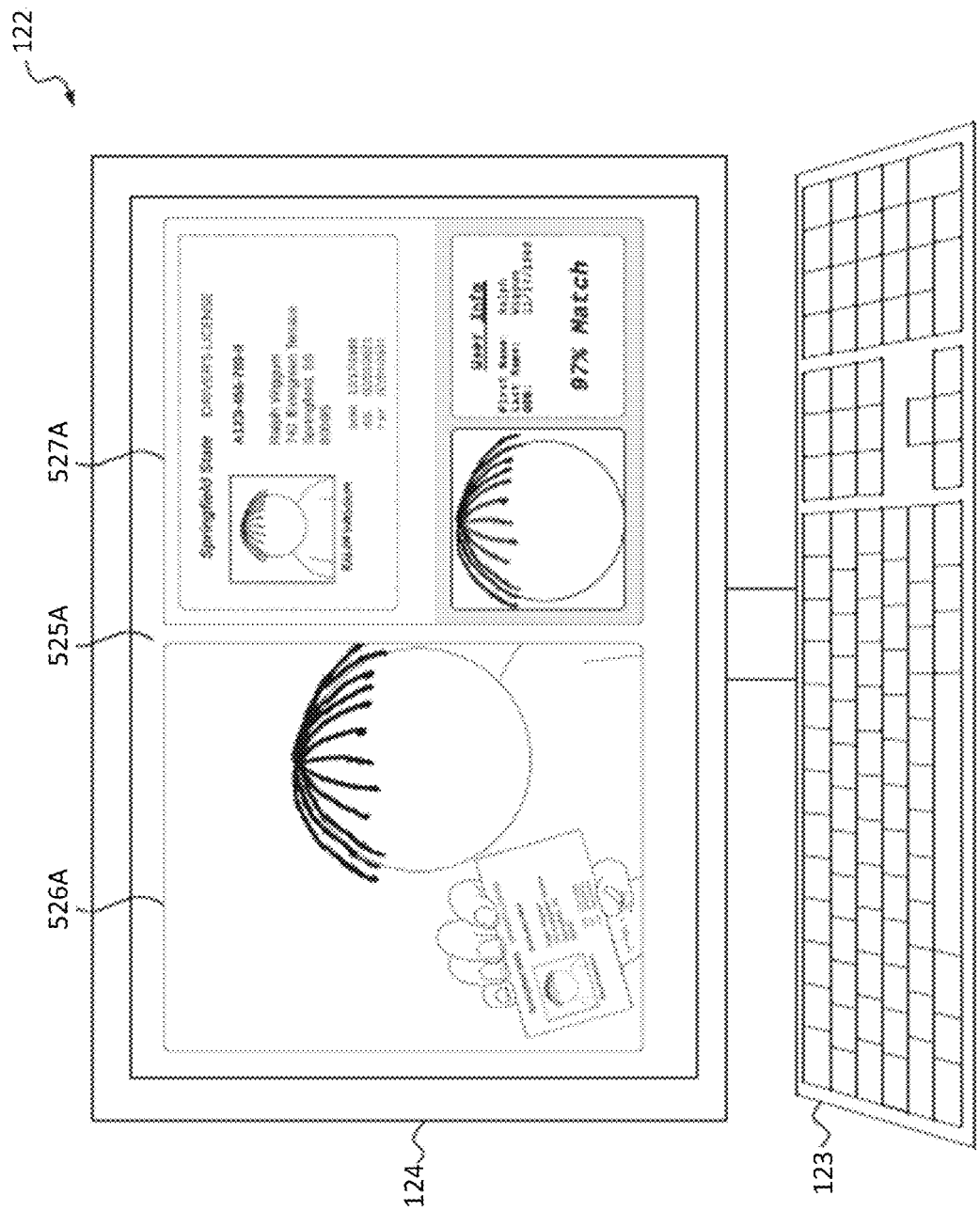
FIG. 5A illustrates an example embodiment of a proctor interface when the user is required to show the user's driver license for identification purposes.

FIG. 5A illustrates an example embodiment where the proctor computing device 122 includes the input device 123 and the output device 124. The output device 124 displays the test user interface 525A which includes a live video feed interface 526A and a proctor assist tools interface 527A. As shown, the test user 101 may present photo identification for user verification, for example as may be performed at steps 212 and 232 of FIG. 2. In some embodiments, the system may extract a region of interest which may correspond to, for example, the test user's photo identification as presented through the live video feed interface 526A. The system may perform blocks 404, 406, and 408 of FIG. 4 to generate a composite image which may correspond to the test user's photo identification, which may be presented through the proctor assist tools interface 527A. Additionally or alternatively, a region of interest may correspond to the test user's 101 face. In some embodiments, no further processing may be applied to the ROI corresponding the test user's face. In other embodiments, blocks 404, 406, and 408 of FIG. 4 may be used to generate a composite image of the user. In some embodiments, the composite image of the test user's photo identification and the composite image of the test user (or a single image of the test user extracted from the video feed 526A) may be utilized to generate a score indicative of a level of confidence that the person shown in the photo identification is the test user.

Figure 5B:
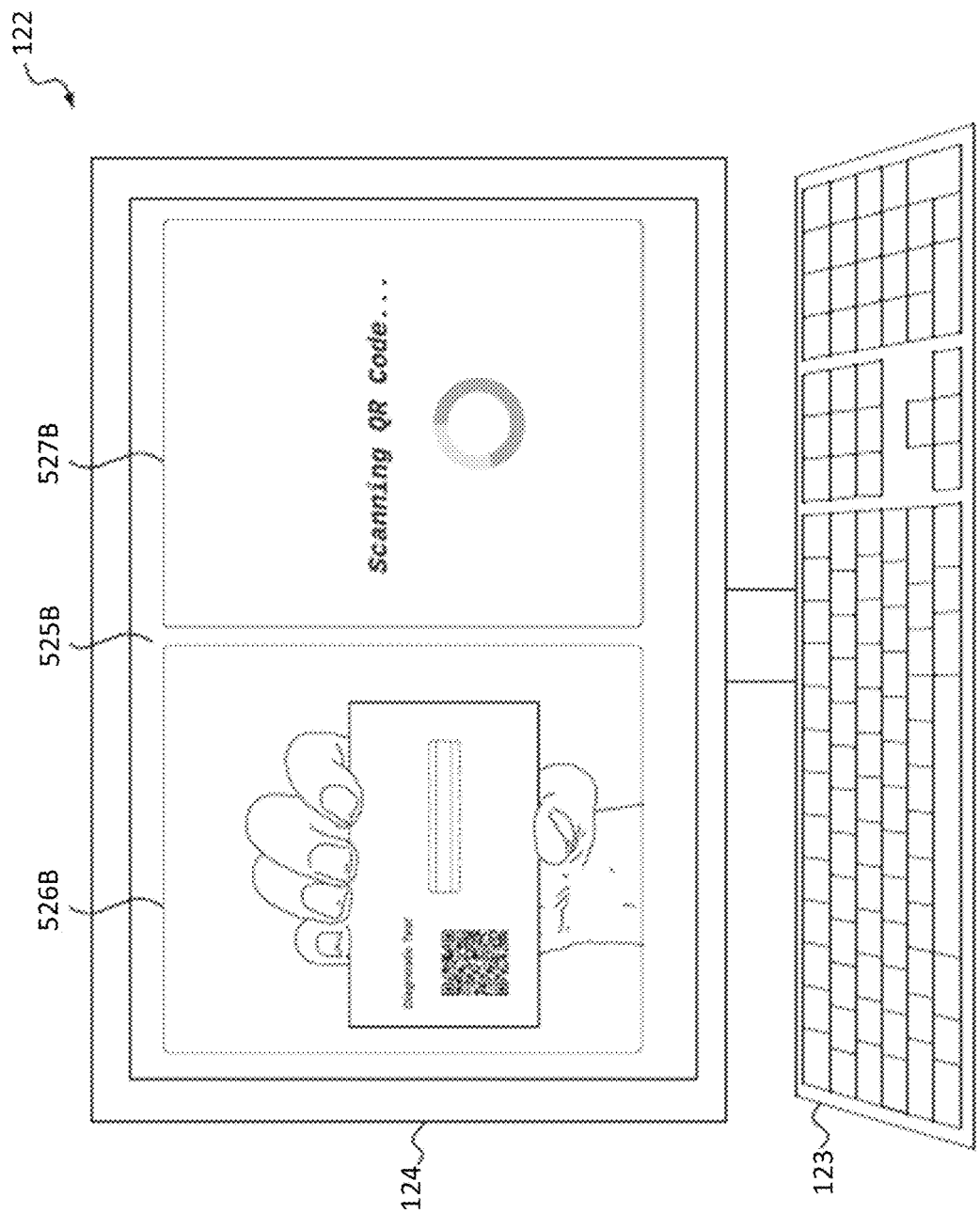
FIG. 5B illustrates an example embodiment of a proctor interface when the user presents the test's QR code.

FIG. 5B illustrates an example embodiment where the proctor computing device 122 includes the input device 123 and the output device 124. The output device 124 displays the test user 101 presenting their diagnostic test to scan a QR code for test verification, for example as may be performed at steps 213 and 233 of FIG. 2. As shown, a test user interface 525B is presented through the output device 124, which includes a live video feed interface 526B and a proctor assist tools interface 527B. In some embodiments, a region of interest may correspond to the QR code presented through the live video feed interface 526B by the test user 101, while the composite image may correspond to an image or scan of the QR code as presented through the proctor assist tools interface 527B that is utilized for querying a database for information associated therewith.

Figure 5C:
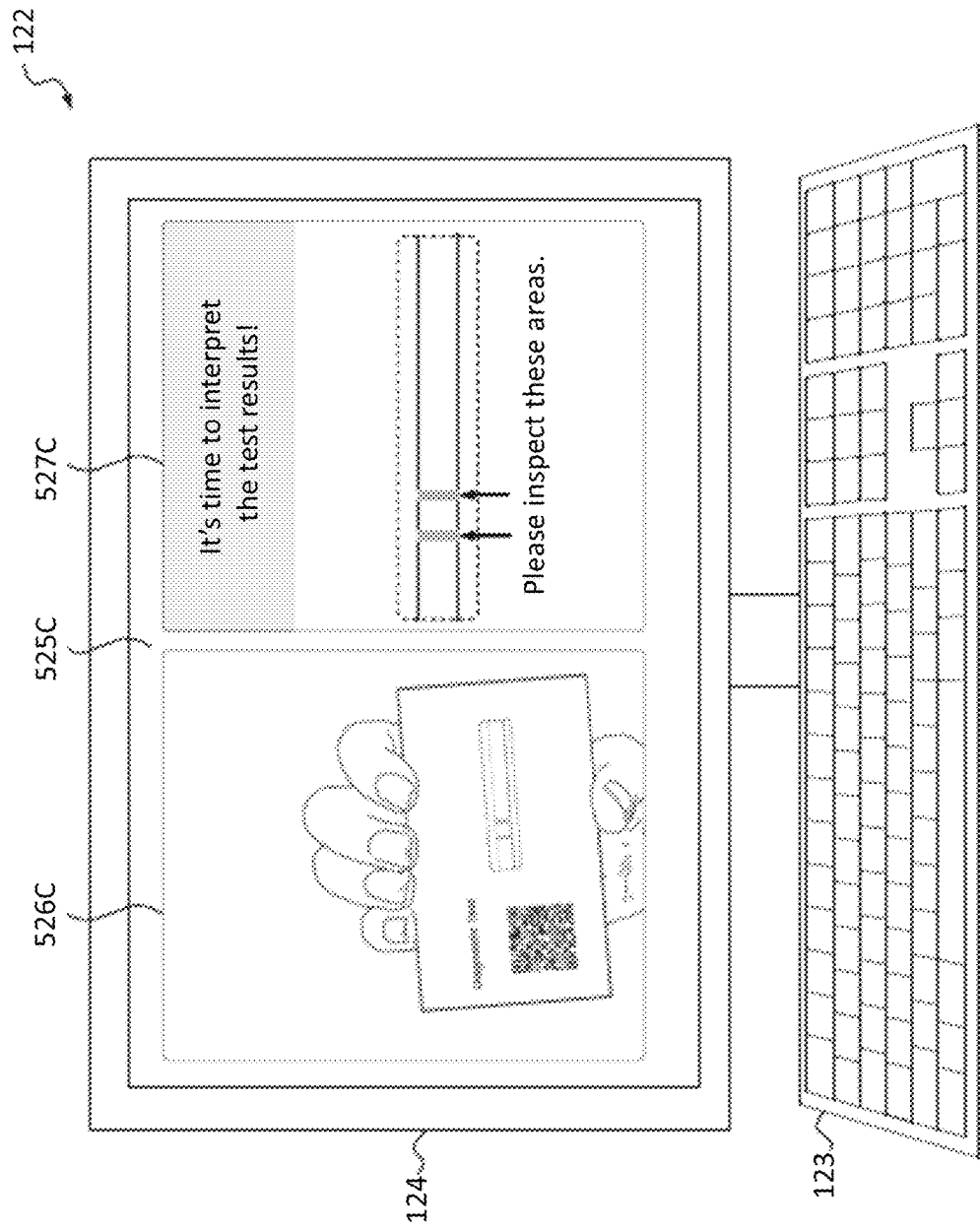
FIG. 5C illustrates an example embodiment of a proctor interface when the user presents their test results.

FIG. 5C illustrates an example of an embodiment where the proctor computing device 122 includes the input device 123 and the output device 124. The output device 124 displays the test user 101 presenting their diagnostic test for test result verification 215, 235. As shown, a test user interface 525C is presented through the output device 124, which includes a live video feed interface 526C and a proctor assist tools interface 527C. In some embodiments, the region of interest may correspond to the test result window of the diagnostic test as presented through the live video feed interface 526C, while the composite image may correspond to the test result window of the diagnostic test as presented through the proctor assist tools interface 527C.

Normalization Techniques

Normalization techniques, for example, as described in this section, can be used to normalize an image or a region of interest (ROI) identified within an image. In some embodiments, the normalization can be configured to normalize, balance, or enhance, illumination levels within the image or ROI of the image. This can help a reviewer of the image (e.g., a proctor) or the ROI of the image to see items within the image or ROI more clearly, thereby facilitating review.

In some embodiments, normalization is only performed on a subset or portion of the image, such as the ROI. That is, normalization may not be performed on portions of an image other than the ROI. Performing normalization on only a portion of the image (e.g., the ROI) can provide several advantages. For example, by normalizing only a portion of the image (e.g., the ROI), the normalization process can be accomplished more quickly than if the normalization process were applied to the entire image. This can allow an enhanced image to be generated and displayed more quickly to the proctor. Another potential advantage associated with normalizing only a portion of the image may be that the result of the normalization is also not influenced by surrounding, less-relevant portions of the image. This can result in higher quality normalization for the ROI. This can occur because the lighting conditions can vary dramatically over different regions of the image and thus can impact the normalization of adjacent regions. Accordingly, in some embodiments, better results can be obtained by normalizing only the ROI. In some embodiments, however, the normalization techniques described herein can be applied to the entire image.

In processing an image, the order of operation in an image processing flow can be important. For example, it can be beneficial to perform identification and/or extraction of the ROI upstream from (e.g., before) the normalization step. This can allow for normalizing only the ROI as noted above.

In some embodiments, normalization of an image or ROI of an image can include applying a kernel to a patch (e.g., a sub portion) of the ROI from an image to calculate a histogram of the patch. In some instances, the peak of the histogram is indicative of the point within the patch of the ROI at which the greatest amount of exposure is exhibited. Normalization can further include adjusting the exposure/illumination level of the patch based on the histogram. For example, the exposure/illumination level of the patch can be increased or decreased. This process can be repeated for additional patches (e.g., sub portions) of the ROI.

The size of the kernel can have a dramatic impact on the normalization result. For instance, for examples in which the ROI corresponds to a test card or some portion thereof, the kernel may ideally be roughly the size of the strip on the test card.

In some embodiments, the size of the normalization kernel can be dynamically adjusted based on the distance between the object to which the ROI corresponds (e.g., test card) and the camera. In some embodiments, such a distance may be determined at least in part based on the size of the object within the image frame. Other techniques for determining and/or estimating the distance can also be used. As the distance between the object and the camera and/or relative size of the object is determined and tracked, the system can dynamically adjust the size of the kernel that is used for normalization processing.

Figure 6:
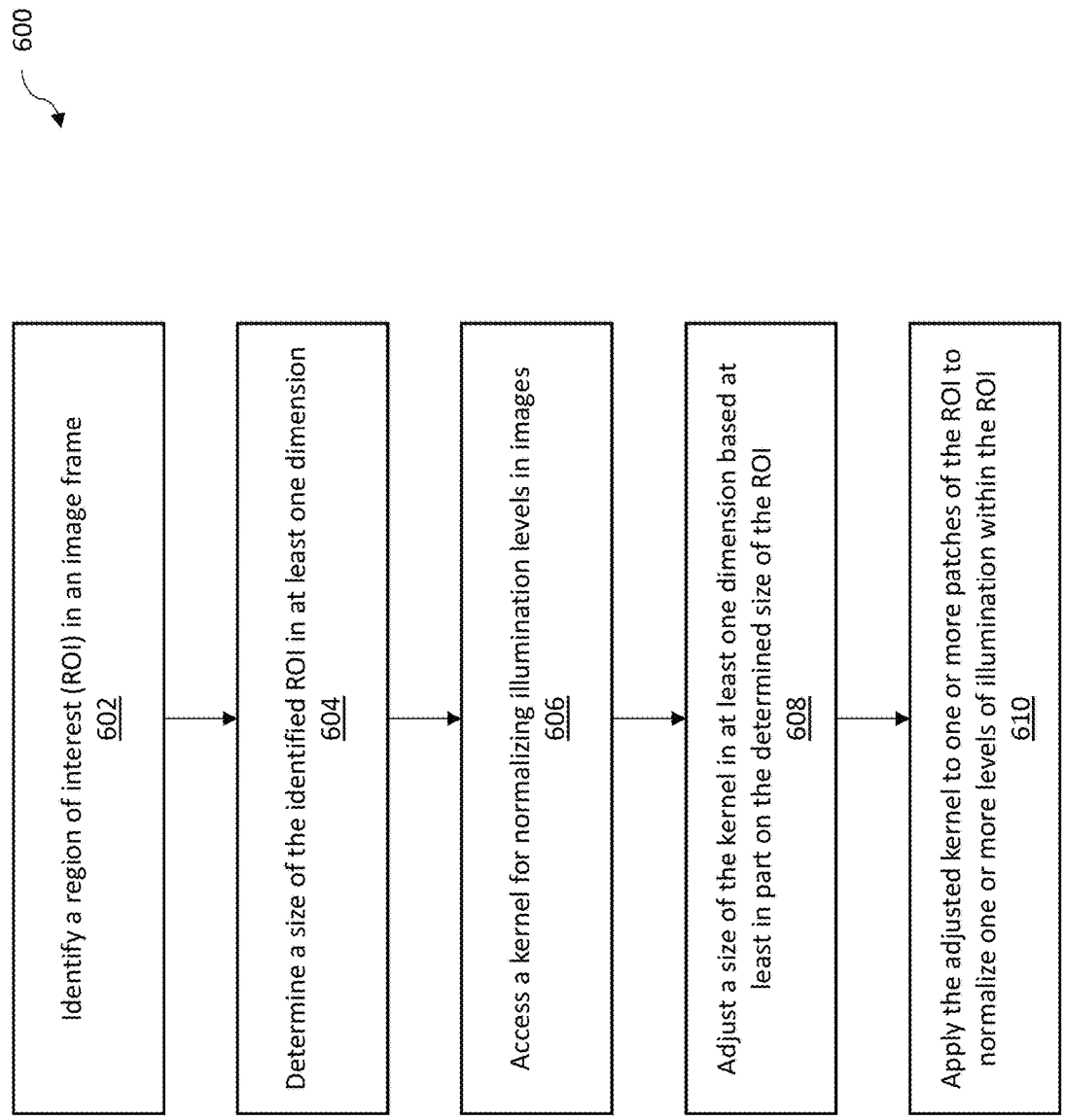
FIG. 6 is a block diagram illustrating an embodiment of a process for the normalization of regions of interest selected from captured image frames.

FIG. 6 is a flowchart illustrating an overview of an example embodiment of a process 600 for normalizing selected portions of a region of interest ("ROI") on an image captured during a proctoring session. In some embodiments, normalization may be performed on patches of the ROI. By only analyzing the ROI rather than the entire image, the speed of the normalization process can be improved. Additionally, the result may not be influenced by surrounding less-relevant portions of the image, which may result in higher quality normalization. In some embodiments, one or more steps of the process 600 may be performed prior to step 402 of the process 400 described above with reference to FIG. 4.

The process 600 may begin at block 602, where a ROI may be identified in an image frame, as captured by a camera. The ROI may correspond to a region of the image frame in which a particular object is shown. For example, the object may be a diagnostic test card or other test material, credential (e.g., an ID), or other items.

At block 604, the size of the identified ROI may be determined in one or more dimensions. In some embodiments, an estimated measure of distance between the particular object and the camera based on the determined size of the ROI may be obtained. For example, the field of view and frustum of the camera may also be taken into account to obtain the estimated measure of distance between the particular object and the camera.

At block 606, a kernel is accessed for normalizing illumination levels in images. For example, the kernel may correspond to a normalization kernel that is stored in memory and accessible to the system.

At block 608, the size of the kernel may be dynamically adjusted in one or more dimensions based at least in part on the determined size of the ROI. In some embodiments, adjusting the size of the kernel in one or more dimensions may be based at least in part on the estimated measure of distance between the particular object and the camera.

At block 610, the adjusted kernel may be dynamically applied to at least one patch of the ROI to normalize at least one level of illumination in the ROI. In some embodiments, the kernel may be utilized to calculate a histogram of the path to apply the adjusted kernel to one or more patches of the ROI to normalize one or more levels of illumination in the ROI. The histogram may be analyzed to identify a peak of the histogram indicative of a point within the patch of the ROI at which a peak amount of exposure is exhibited and an exposure or illumination level of the patch may be adjusted based on the analysis. This may be repeated for each additional patch of image data contained within the ROI until the entire ROI has been analyzed and normalized using the kernel.

Enhanced Video Display

At times, the proctor may be viewing a live webcam feed from a user and may have a need to closely examine information. For example, the proctor may need to carefully examine an identification credential, a lateral flow test reading, and so forth. However, the user's webcam stream will often have a considerable amount of unneeded information that can distract the proctor or take up valuable space. Coupled with the often poor quality of many webcams (e.g., low resolution, poor light sensitivity, large amounts of noise, fringing, and so forth) and sub-optimal conditions (e.g., poor lighting, camera placed too far away, unstable mounting or holding of the device, and so forth), it can be difficult for the proctor to gather information, resulting in increased time to read the information and decreased accuracy.

Figure 7:
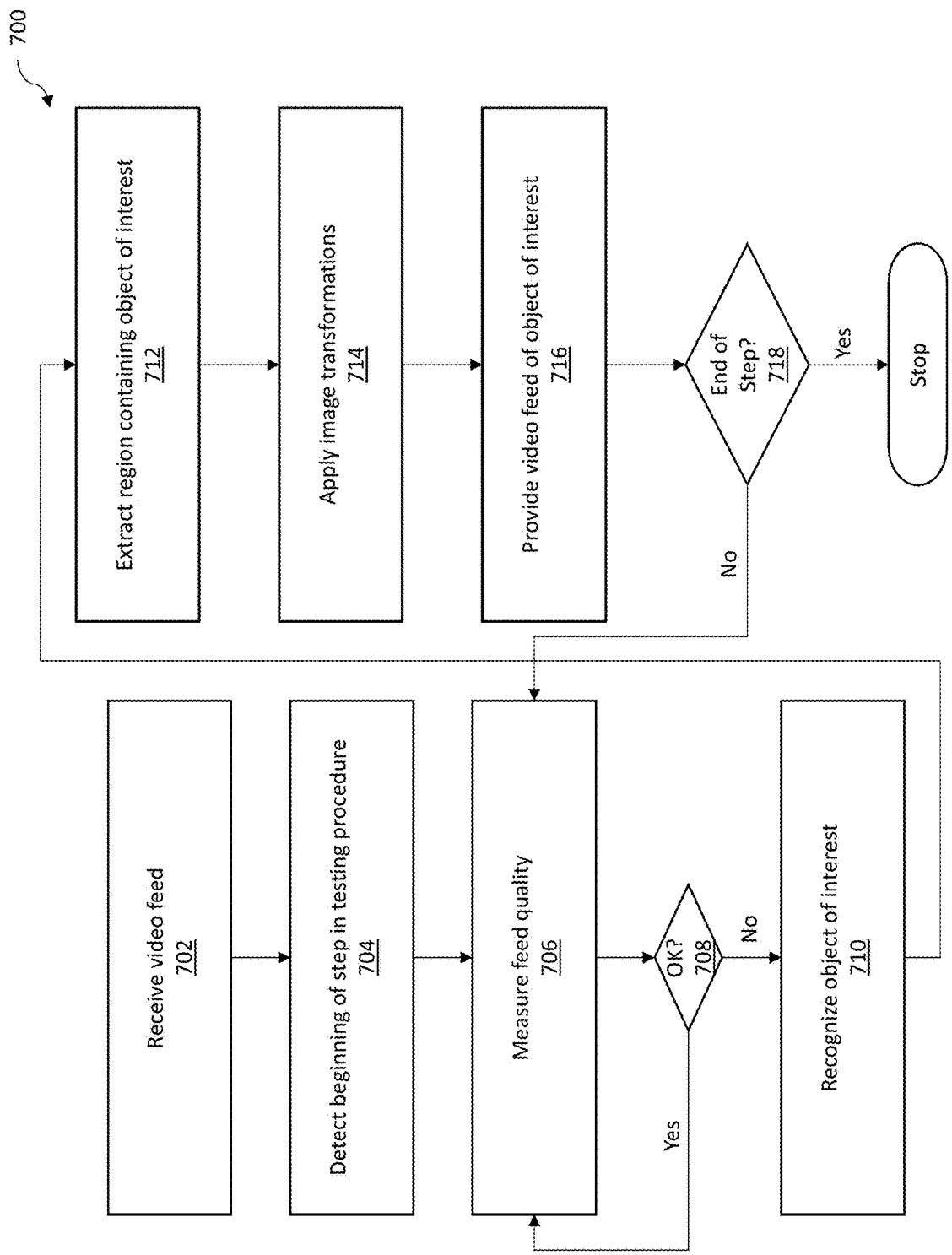
FIG. 7 is a block diagram illustrating an embodiment of a process for enhancing a live video feed during a testing session.

FIG. 7 is a diagram of an example process 700 for enhancing a video feed according to some embodiments. At block 702, a system may receive a video feed from a user. At block 704, the system may detect that the user has reached a particular step in a testing procedure. This may be determined from the video itself, as a result of the user clicking a button, and so forth. At block 706, the system may determine the quality of the video feed and, at decision 708, if the system detects that the video feed quality is acceptable, may continue to monitor the feed or if the system detects that the video quality is not acceptable, may recognize an object of interest at 710. The system may, at 712, extract a region of the video feed that contains the object of interest. At 714, the system may apply one or more image transformations to the extracted region of interest and at 716, the system may provide a video feed of the object of interest to a proctor. At decision 718, the system may determine if the user has completed the particular step. If the user has not completed the particular step, the system may continue to measure the feed quality and provide a transformed video feed upon detecting that the feed quality is below a threshold quality. If the video feed is acceptable, the system may stop providing the transformed video feed.

In some embodiments, an overlay may be provided to the proctor containing information from the live webcam feed. In some embodiments, a system may determine frame quality (e.g., blur, compression artifacts, time since last frame, and so forth) to determine whether to display an overlay. The system may use feature matching (for example, Oriented FAST and rotated BRIEF (ORB) or scale-invariant feature transform (SIFT) to find correspondences between frames of the live webcam feed and a high quality template of an object of interest (for example, a license or test strip). In some embodiments, the system may use stabilization techniques, white balancing, and/or denoising algorithms to improve the quality of images from the live webcam feed. In some embodiments, the system may have templates with details such as the locations of key information (e.g., the location of the user's date of birth on a driver's license issued by a particular state).

Figure 8:
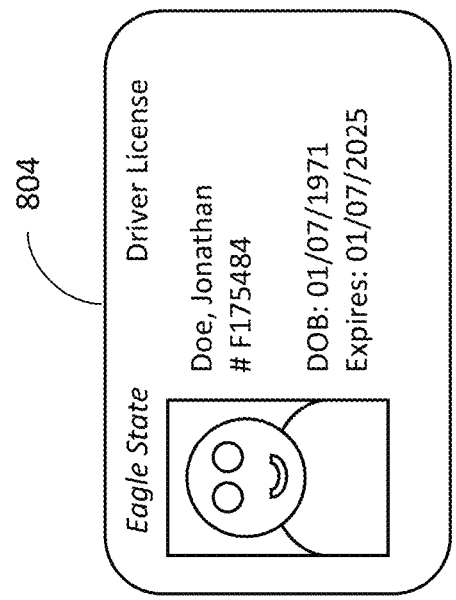
FIG. 8 is an illustrative example of video enhancement according to some embodiments herein.
Figure 8:
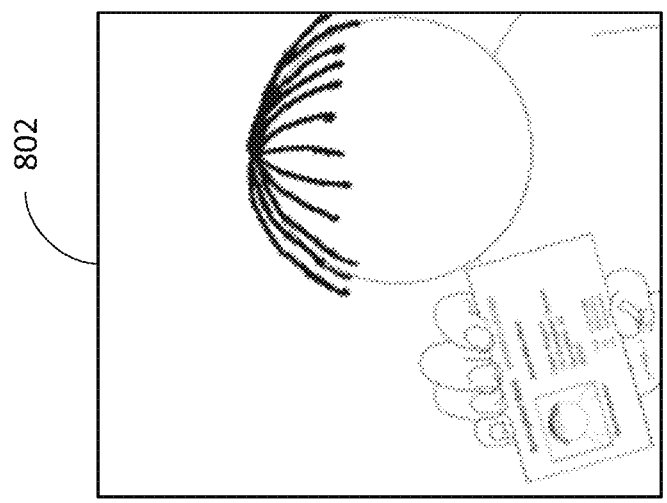

The overlay may provide the proctor with a normalized, large, clearly readable display containing a live feed of the object of interest. Because the proctor is presented with a feed rather than a single image or a composite image, the proctor may be able to fill in any information many from a particular frame based on other frames that the proctor has observed. The overlay may be presented to the proctor in a manner similar to that shown in FIG. 5A, with still images replaced by video feeds. Alternatively, in some embodiments, the original video feed may be replaced by an enhanced video feed. For example, as depicted in FIG. 8, the original video feed 802 may contain an object an interest (e.g., a driver's license) that is shown at a small size and low quality. The system may extract the portion of the video containing the driver's license or other object of interest, enhance the video, and display a replacement feed 804 that shows a clear video of the object of interest that the proctor can easily read.

Proctor Judgment Evaluation

In some embodiments, a system (e.g., a proctoring or testing platform) can be configured to evaluate a proctor's ability to correctly interpret a test result under current testing conditions. Based on this evaluation, the proctor may be provided with suggestions and/or notifications that may serve to aid the proctor in interpreting test results and/or taking action to improve current conditions such that the likelihood of correct test result interpretation may be increased.

For example, the systems can determine whether, under current testing conditions, the proctor is more or less likely to make an accurate determination of test results. In the event that the system determines that the current conditions decrease the likelihood that the proctor can make an accurate determination of the test results, the system can provide the proctor with instructions for improving the current conditions in order to increase the likelihood of an accurate determination. In general, the system may determine the level of confidence in the proctor's ability to correctly interpret a test result under current conditions and determine whether to provide the proctor with assistance based on the level of confidence (e.g., by way of providing the proctor with helpful suggestions and/or other information).

In some embodiments, the system can generate one or more assurance or confidence levels that can be considered singly or in combination in determining an overall confidence or assurance level related to the proctor's ability to accurately interpret test results under the current conditions. Such one or more confidence levels can include one or more of a test result assurance level, a lighting quality assurance level, an image quality assurance level, and/or a distance assurance level, among others. In some embodiments, the test result assurance level comprises an overall level that is determined based upon one or more other levels.

The test result assurance level can be configured to provide an "alert level" associated with current testing conditions. For example, if current testing conditions create a condition where there is an unreasonably high chance of an improper test result determination, an alert can be provided to the proctor. Such an alert can indicate to the proctor that extra care must be taken or that certain steps should be taken to improve the current testing conditions. In some embodiments, the alert level may correspond to a confidence score that is generated based on any of a variety of factors, including one or more of those discussed below (e.g., lighting, image quality, distance, etc.). This confidence score can be indicative of the system's level of confidence in the proctor's ability to accurately read and/or interpret the test result.

The test result assurance confidence level can, in some embodiments, be compared to thresholds. Depending upon where the confidence level falls relative to the threshold, the system can determine what should be communicated to the proctor.

In some embodiments, the system may also determine whether it believes that the test result is positive or negative. For example, computer vision or other artificial intelligence methods can be used to read the test result. However, this determination may not be shared with the proctor in all embodiments. Rather, whether the proctor's determination matches the system's determination of the test result can be a factor in determining the test result assurance confidence level. Further, in some embodiments, the system can also generate a confidence score that is indicative of the system's level of confidence in the test result as determined by the system (level of confidence in its own test result interpretation).

One or both of the aforementioned confidence scores can be generated and considered to determine (i) the aforementioned alert level, (ii) whether or not any messages should be provided to the user and/or proctor and the nature of such messages, etc. The messages provided to the user and/or proctor can be configured to provide guidance in improving current testing conditions, thereby improving the overall test result assurance confidence level and increasing the accuracy of the test. For example, by following and/or considering the suggestions that are provided, the proctor can take action to lower the overall alert level below a threshold value such that the testing conditions are deemed to be sufficient.

A lighting quality assurance level can be determined based on data indicative of the lighting conditions in the testing environment to the proctor. For example, an image from which a test result will be determined can be analyzed to determine whether the lighting conditions are sufficient for such a result. If the image appears too dark or too light, then the lighting quality assurance level can be decreased. The lighting quality assurance level can be a factor considered in determining the overall test result assurance confidence level.

An image quality assurance level can be determined based on data indicative of the rate of image compression, network speed, etc. to the proctor. For example, network parameters can be analyzed to determine if the video feed a proctor is reviewing is of sufficient quality to allow for an accurate determination of a test result. The image quality assurance level can be a factor considered in determining the overall test result assurance confidence level. In some embodiments, the image quality assurance level can be determined by or be based on the quality and/or quantity of information sent between the user and the proctor, such as information that is communicated over the internet. In some instances, a network connection may place hard limits on how much information can be conveyed to the proctor. Both the proctor's and the user's connections can be evaluated.

A distance assurance level can be determined based on data regarding the distance between the user and the camera.

For example, an image of the user and or the testing materials can be analyzed to determine how close the user and testing materials are to the camera. If the user and/or the testing materials are too far or too close to the camera, it may be difficult to correctly interpret the result, causing a decrease in the distance assurance level. The distance assurance level can be a factor considered in determining the overall test result assurance confidence level. In some embodiments, the distance assurance level can be determined by the system based on a known resolution of the user's camera and the rate of compression. From this, the system can calculate how close to the camera the user needs to be in order to achieve an acceptable level of signal-to-noise. In some embodiments, this can further be determined based on the frustum or field of view of the user's camera and how large the ROI is in the frame.

Figure 9:
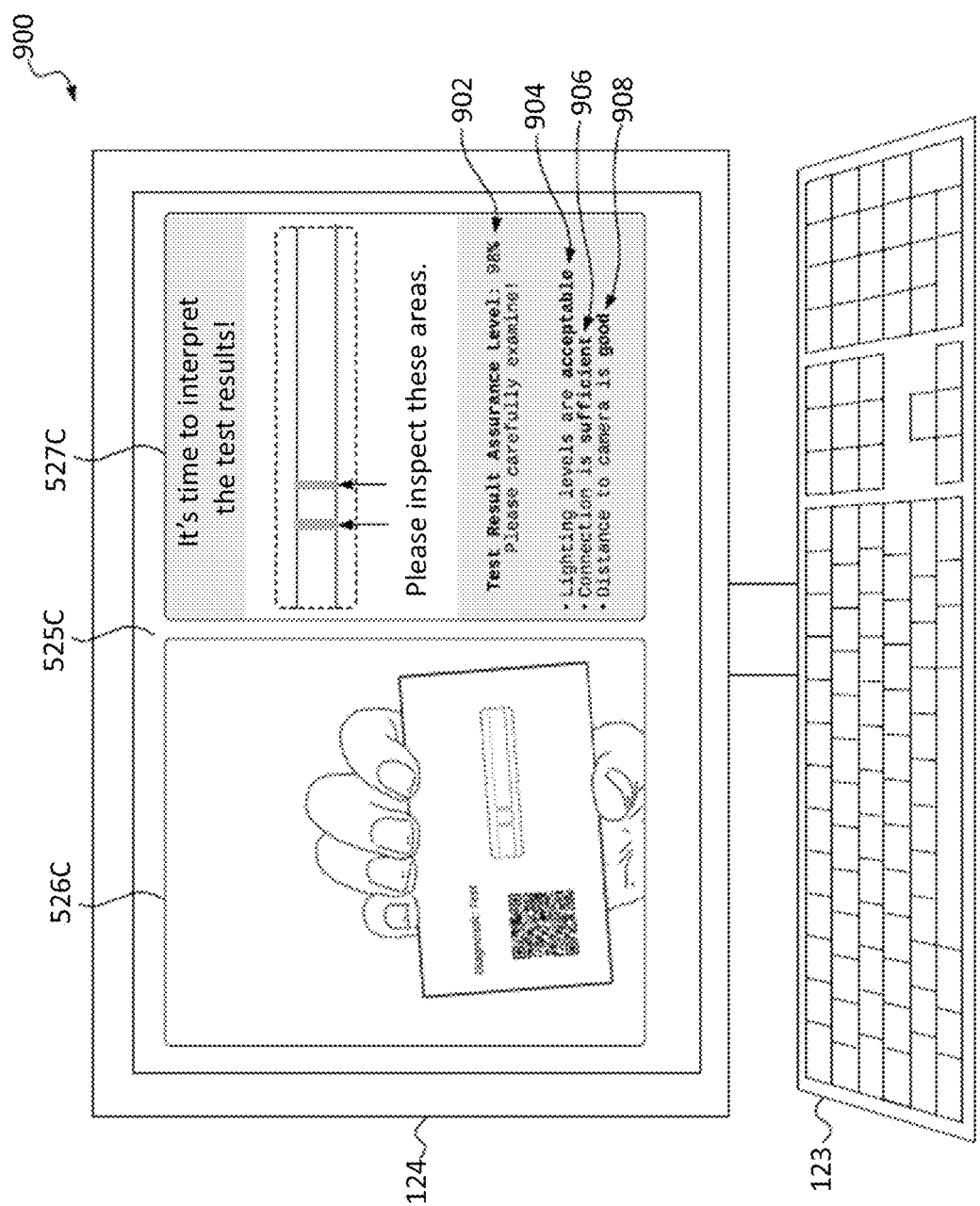
FIG. 9 illustrates an example embodiment of a proctor interface including a test result assurance level according to an embodiment.

FIG. 9 illustrates an example embodiment of a proctor interface 900 including a test result assurance level 902 according to an embodiment. The test result assurance level 902 can be an indication determined as described above that relates to how likely the proctor will be able to accurately interpret test results given the current conditions. In the illustrated embodiment, the proctor interface 900 also includes a lighting assurance level 904, an image quality assurance level 706, and a distance assurance level 908. In some embodiments, if any of the lighting assurance level 904, the image quality assurance level 906, and the distance assurance level 908 are determined to be insufficient, the proctor can be provided with alerts or suggestions that can be used to improve the related condition, such as recommending that the user move closer, turn on a light, and so forth.

In some embodiments, the system can further be configured to evaluate how well the proctor is doing (e.g., in comparison to their peers). Additionally or alternatively, the system can further be configured to evaluate how well the proctor is doing compared to a computer vision or artificial intelligence determination of the test results. That is, the results as interpreted by the proctor may be compared with the results as determined by the system to determine a level of performance. This can operate on the assumption that the AI/CV of the system is more accurate than the user. This level of performance can also be used by the system in generating the confidence score indicating its level of confidence in the proctor's ability to correctly interpret the test results (i.e., the confidence score may depend on the individual proctor, not only external factors such as lighting, image quality, and distance). The proctor's performance may also hinge on any of the above factors. For instance, even though the proctor's interpreted result may disagree with that of the system, if the testing conditions were horrible, then the proctor's performance should not necessarily be seen as sub-par. In some embodiments, heuristics can be used to normalize proctor scores and ratings. Proctor suggestions may also be throttled based on any of a variety of factors, such as proctor experience/tenure. For instance, a new proctor may find such suggestions to be quite helpful, while a more experienced proctor may find such suggestions to be annoying.

Proctor Time Reduction

Figure 10:
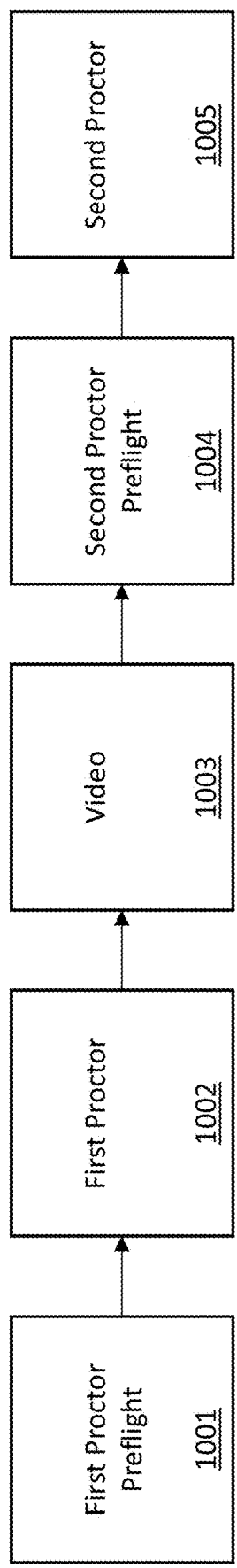
FIG. 10 illustrates an example testing process according to some embodiments.

FIG. 10 illustrates various steps in a testing session according to some embodiments. As shown, the testing session may include a first proctor preflight portion 1001, a first proctor portion 1002, a video portion 1003, a second proctor preflight portion 1004, and a second proctor portion 1005. In some embodiments, the preflight portions 1001 and 1004 include certain steps that are performed by the user prior to being joined by the proctor. These may include steps for which a proctor is not needed such as, for example, confirming login information, providing instructions in case the user gets disconnected during the testing session, providing instructions for adjusting the user's camera, providing an overview of the testing procedure, unpacking a testing kit, scanning a QR code or other identifier of the testing kit, performing preparatory steps such as adding drops of solution, performing particular steps (e.g., nasal swabbing), inserting the nasal swab into a solution, displaying a test result to the camera, and so forth.

In some embodiments, the time spent by a proctor in a test flow can be reduced by mandatory or optional preflight videos or portions for first-time users and/or repeat users. Repeat users may be provided with streamlined, less verbose scripts. In some embodiments, some steps in the test flow may be moved into an automated preflight experience or portion that may not require a proctor. In some embodiments, these changes to the test flow may reduce median proctor time per session by about one tenth, about one fifth, about one fourth, about one third, about one half, any number in between, or even more, depending on how much of the test process is automated.

A preflight video, which can be for all users, first-time users, and/or repeat users, can be advantageous. In some embodiments, a video may be targeted at first-time users. For example, certain diagnostic tests may include several steps that can be confusing for first-time users. If a user is seeing instructions for something completely new to them and listening to the proctor simultaneously, additional proctor time may be needed. Presenting a short video (for example, about a few minutes) that explains the test process prior to the user interacting with a proctor may reduce the time proctors spend guiding users through the test process.

In some embodiments, such a video may be presented from a first person perspective (e.g., so that the video shows what the user will see). In some embodiments, the video may be presented from another perspective (e.g., third person). Some portions of the video may be presented from other perspectives (e.g., third person). As an example, a portion of the video showing swabbing of the nose may be shown in a third person view. It may be advantageous for the video to be short in duration, for example less than 5 minutes, less than 4 minutes, less than 3 minutes, less than 2 minutes, or less than one minute. In some embodiments, the video may include a voiceover and/or closed caption for all or some steps.

Figure 11:
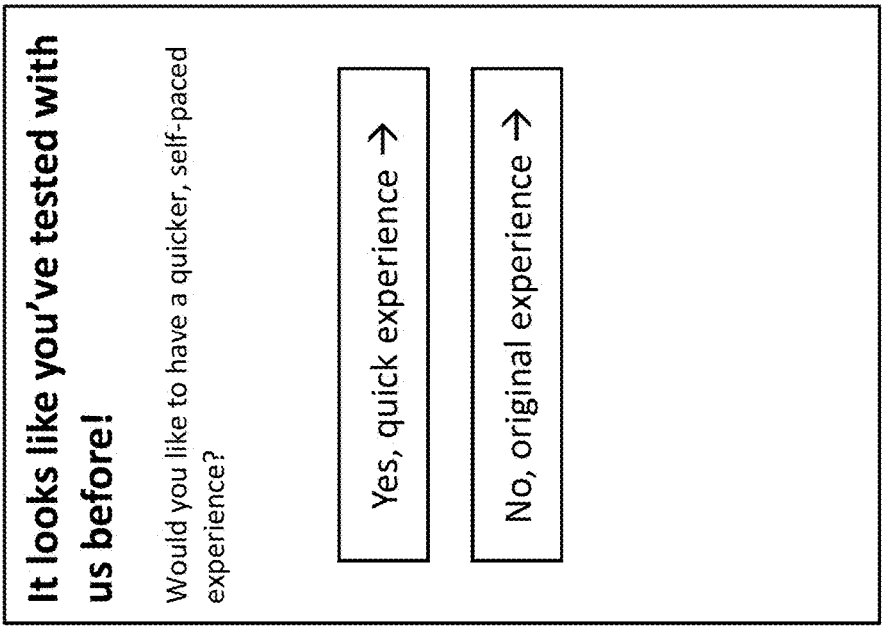
FIG. 11 illustrates an example embodiment of a user interface that may be presented to repeat users according to some embodiments.

During some portions of a proctored testing session, repeat users who are familiar with the process may be presented with a streamlined experience which may include less verbose scripts. For example, as shown in FIG. 11, a repeat user can be prompted to either engage with a quick or streamlined experience or to proceed with the original or full experience. The streamlined experience can be advantageous because once many users have taken a test at least once, they often complete steps before the proctor is done reciting the script. Reducing the length of the script will reduce the proctor bottleneck for these users, speeding the test experience for users and reducing the time proctors spend explaining the procedure to users who already know how to perform the testing procedure.

As noted above, it may be advantageous to provide a non-proctored preflight portion prior to a proctored portion of a testing experience. These can be related to steps that users can perform on their own to set up for a proctored interaction. For example, as shown in FIG. 10, there are several steps at the beginning of the first and second proctor sessions that can be automated without regulatory impact. Any part of the experience that a user can complete in a self-guided manner directly reduces proctor time.

In some embodiments, a preflight process can include, for example, part or all of identity verification, checking for the correct test (for example, by checking the test box), checking device setup (e.g., camera angle, positioning, audio functionality, etc.), unpacking and verifying test components, initial test card code scan, subsequent test card code scan, capturing a results image, and/or result explanation and self-attestation, as well as other steps.

In some embodiments, each automated step may include a proctor fallback in case the user fails to complete the automated steps or encounters difficulty completing the automated steps.

In some embodiments, a preflight experience may comprise an augmented reality (AR) pre-flight check that briefly guides the user through the testing process to show the user what to expect during the testing session. In some embodiments, an augmented reality pre-flight check can occur before a user is connected with a proctor. In some embodiments, users or potential users may be able to follow the augmented reality pre-flight check prior to signing in, while in other embodiments only users who are signed in may be able to view the pre-flight check. In some cases, a potential user may want to get an idea of how the testing process works before deciding to use a remote testing platform. The pre-flight check may help the user get ready for testing, may reduce proctor call times, may improve user comfort by showing the user what to expect, and may provide marketing opportunities to showcase the capabilities of the remote testing platform and/or related products. For example, if the testing service also provides prescription delivery, the prescription delivery service may be marketed during the pre-flight experience.

In some embodiments, a testing platform may be deployed on a computing system and may provide an augmented reality pre-flight check, which may comprise a short AR-based guide (e.g., about 30 seconds, about 45 seconds, about 60 seconds, or about 120 seconds, or any number between these numbers, or more or less). The system may be configured to instruct a user to scan their environment with a camera, and the system may identify areas of the user's surroundings that are suitable for use during the testing process. For example, the system may utilize computer vision and/or artificial intelligence/machine learning models to identify a flat surface that is large enough for use during the testing process. In some embodiments, an artificial intelligence or machine learning model may be trained to recognize objects and surfaces in a room by, for example, collecting a set of images or videos from a database (e.g., captured video or images from prior testing sessions or from another source such as an available database of room photos), applying one or more transformations to each image or video (for example, mirroring, rotating, smoothing, reducing or increasing contrast, reducing or increasing brightness, denoising, and so forth) to create a modified set of images or videos for training, creating a first training set comprising the collected set of images or videos, the modified set of images or videos, and a set of non-pertinent images (for example, landscapes, portraits, and so forth), training the model using the first training set, creating a second training set containing the first training set and non-pertinent images that were misidentified during the first training, and performing a second training of the model using the second training set.

In some embodiments, the system may identify an area for use during testing and may recommend that the user remove one or more items from the area. For example, the system may identify a flat surface that is suitable for testing but that has one or more items that should be removed from the area. Alternatively, a user may use their device to take a picture or video of an area or surface to use during testing. The system may analyze the captured images or videos to check that the area meets certain requirements, such as size and orientation. In some embodiments, the system may use other data from the user's device, such as the orientation of the device, which the system may use to determine if a surface is parallel to the floor or within a suitable angle with respect to the floor. In some embodiments, the system may use depth information from the user's device to help determine the size of an area or other objects. In some cases, depth data may not be available. For example, the user may be using a device that lacks a depth sensor or the information received from the user may lack depth data for some other reason. In some embodiments, AR content may be overlaid onto the image to show the required size so that the user may compare the space to the required space.

In some embodiments, the system may set the selected area or surface as an anchor relative to which other AR content may be generated. The system may, for example, suggest a location for the user to place their phone or other device based on collected images of the user's environment. In some embodiments, the system may check that the arrangement allows sufficient viewing of the selected surface.

In some embodiments, the system may generate AR content to show a photo identification document and/or a test box on the selected surface. In some embodiments, the system may generate AR content associated with each component within the test box. In some embodiments, the system may demonstrate each step of the test to the user. In some cases, the system may provide narration and/or text-based guidance to the user. In some embodiments, the system may generate AR content to show possible outcomes of the test and/or to provide information about treatment availability.

In some embodiments, data may be tracked and/or user input may be requested so that the full pre-flight experience is provided to new users while an abbreviated version is provided to repeat users. In some embodiments, the system may determine a type of experience to provide based at least in part on determining whether the user's device is suitable for providing an AR experience. For example, a user with a smartphone may be able to use an AR experience, while such an experience may not be suitable for someone using a desktop computer.

Figure 12:
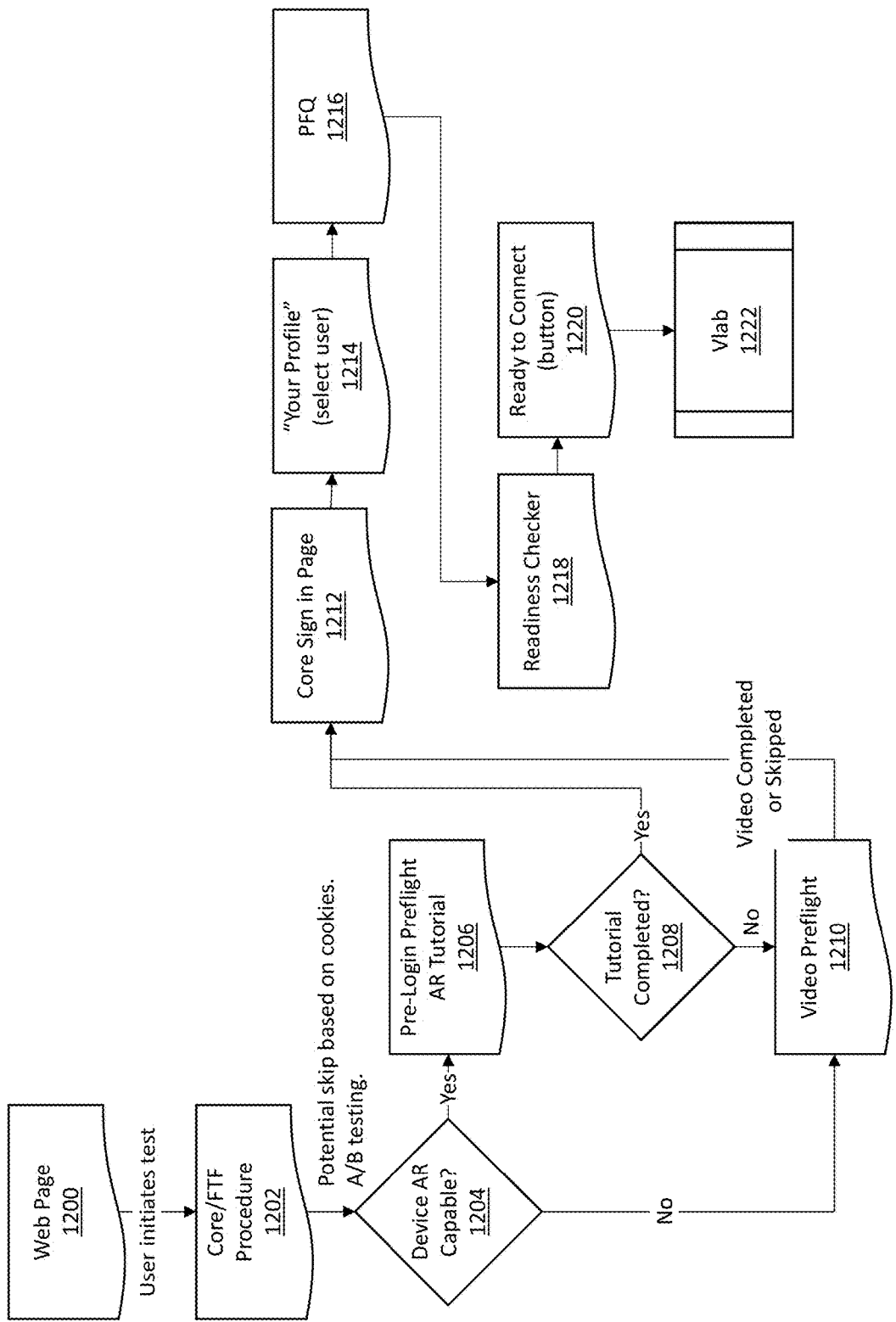
FIG. 12 is a block diagram illustrating an example tutorial and test preparation process according to some embodiments.

FIG. 12 depicts an example process flow according to some embodiments that may be deployed on a computing system. At 1200, the system provides a web page for viewing by a user. In some embodiments, the web page may be a generic web page provided by a provider of a testing process. In some embodiments, the web page may be a customized or branded portal. For example, the web page may be branded or otherwise customized to meet the desires of a healthcare provider system, a health insurance company, a state or local government entity, and so forth. At 1202, after the user initiates testing, the system may conduct one or more procedures, which may include determining capabilities of the user's device. For example, the system may determine if the user is using a smartphone, a desktop, or a laptop, and may adjust the experience accordingly. In some embodiments, the system may use information about the operating system, screen resolution, available cameras, memory, processor, and so forth to help determine what type of experience to provide to the user. At 1204, if the user's device is capable of providing an AR experience, the system may provide the user with a pre-login preflight AR tutorial at 1206. If the user does not complete the tutorial, then at 1208, the system may direct the user to a preflight video 1210. At 1204, if the user's device is not capable of providing an AR experience, the system may direct the user directly to the preflight video 1210. If the user completes the tutorial at 1208 or the user is shown the preflight video 1210, the system directs the user to a sign in page 1212. The user may then be shown a user selection page 1214 that allows the user to select the person taking the test. At 1216 and 1218, the system may conduct procedures to ensure that the user is ready to proceed with a proctored testing session and to ensure that there is a proctor available for the testing session. At 1220, the system may present the user with a button, link, or the like to proceed to the proctored testing session. At 1222, the system may provide the user with a proctored testing session.

In some embodiments, one or more steps may be skipped. For example, in some embodiments, cookies may be used to determine that a user has previously engaged in testing or the AR tutorial, and the system may skip the AR tutorial and direct the user to the core sign in page 1212. In some embodiments, a system may be configured for performing A/B testing. For example, some users may be directed to the preflight video 1210 instead of the AR preflight 1206 even though their device is AR capable. This testing may be useful for a variety of purposes, for example to determine the effectiveness of one preflight type vs. another (e.g., AR vs video). The information may be used to improve a preflight experience.

Figure 13:
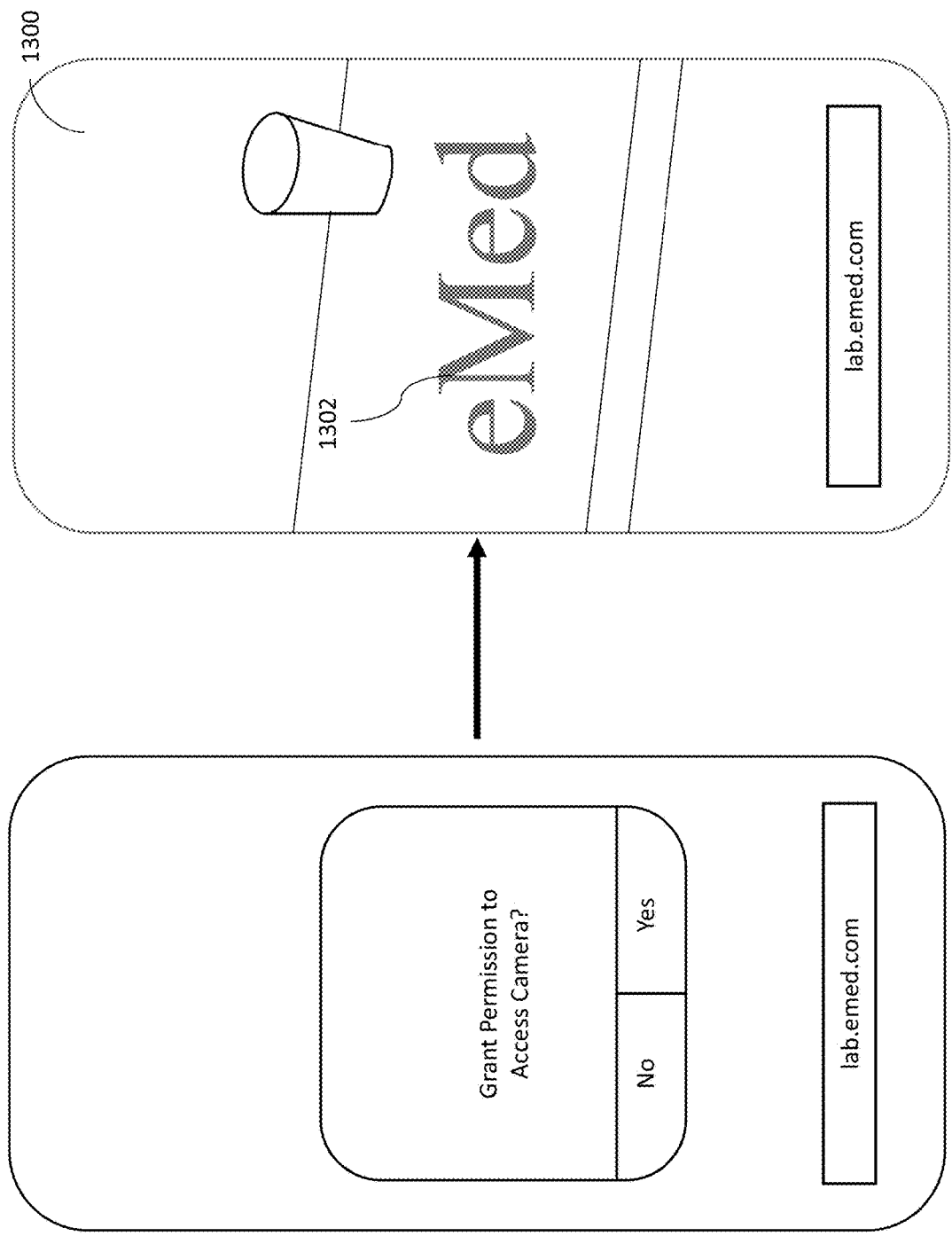
FIGS. 13-18 are example illustrations of some augmented reality tutorial steps according to some embodiments herein.
Figure 14:
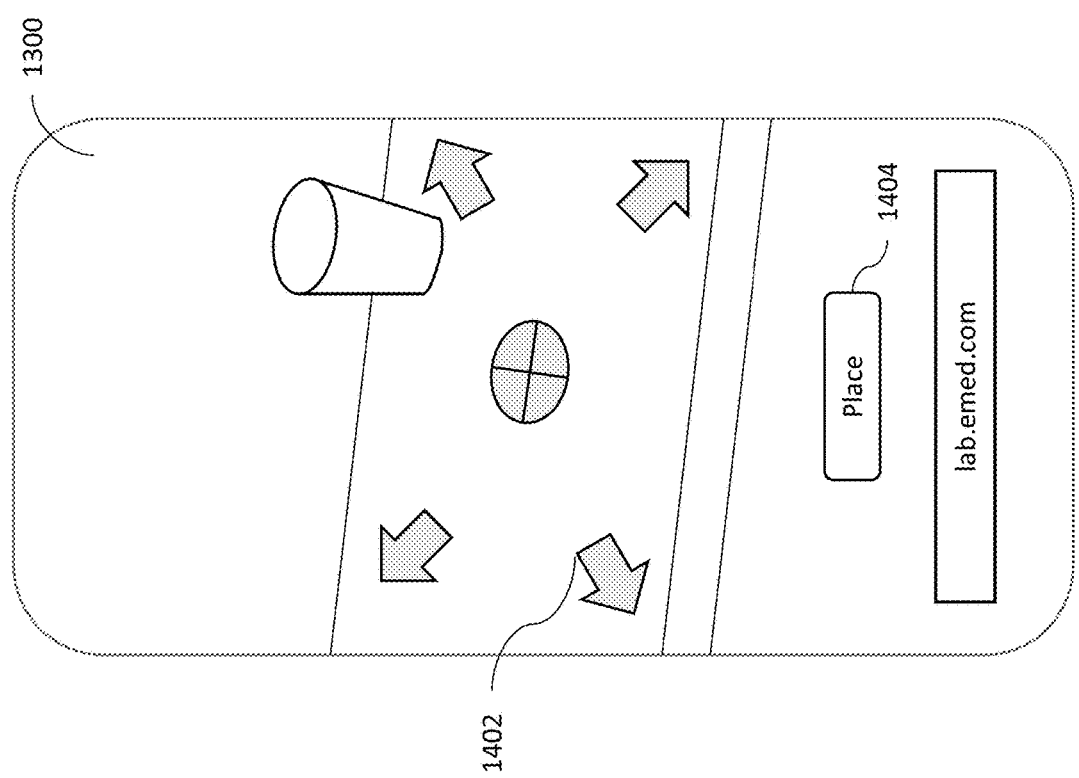
Figure 15:
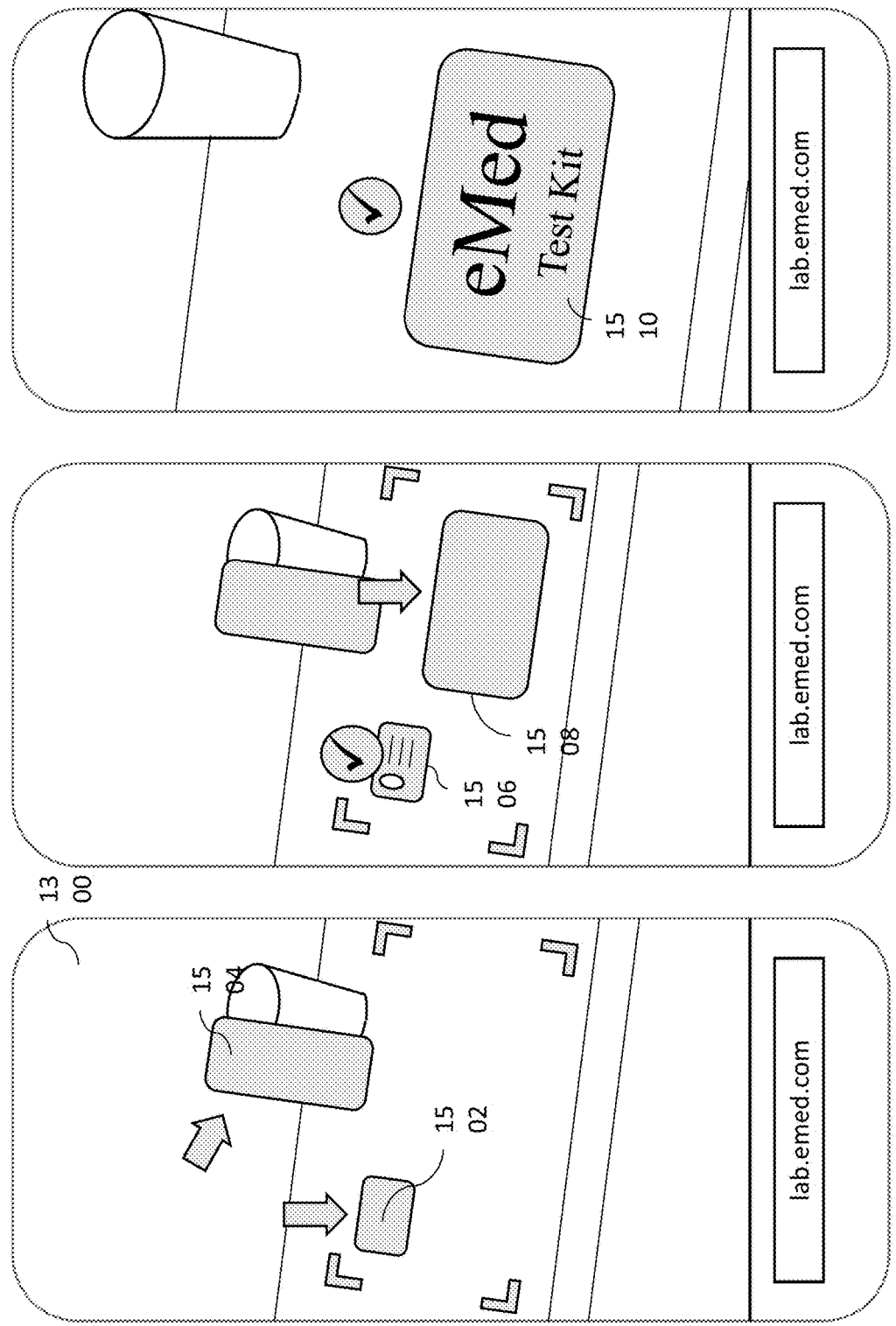

FIGS. 13-18 and 20-21 show an example AR pre-flight experience according to some embodiments. In FIG. 13, the system may ask the user for permission on a supported device. For example, the system may need access to the camera in order to provide an AR experience. Once the user grants permission, the system may provide a greeting such as, for example, a voice greeting from a virtual assistant or a pre-recorded message. The system may display a view 1300 of the user's environment with an overlay greeting 1302. In FIG. 14, the system may prompt the user to define an anchor point of a surface for the remainder of the AR experience, for example by displaying an AR overlay 1402 on a surface and asking the user to tap a button 1404 to confirm the anchor point. The virtual assistant or a pre-recorded message may suggest that the user clear the surface of any objects that may get in the way of testing, such as pens, papers, headphones, decorations, etc. that may be placed on a desk, table, or other surface. In FIG. 15, the system may overlay virtual elements on a view of the surface to show the user how to get ready for the testing session. For example, the system may show indicators 1502, 1504, and 1508 to guide the user in placing items such as the user's identification, cell phone or other device, and test kit. The system may illustrate successful placement by, for example, showing an AR checkmark and representation of an identity card 1506 and/or an AR checkmark and test kit 1510.

Figure 16:
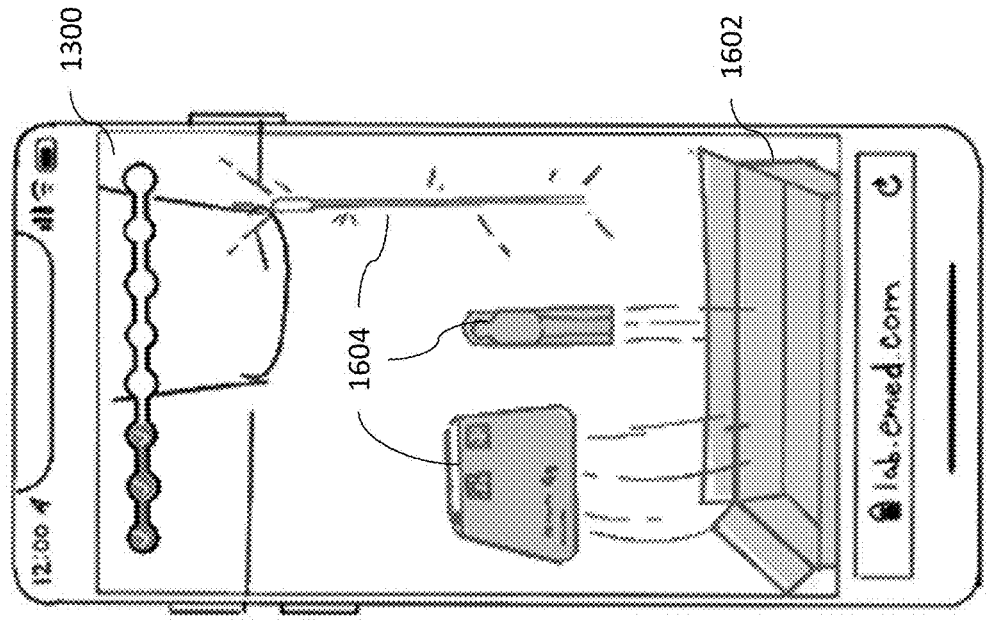

In FIG. 16, the system may display AR content depicting the test box 1602 in an open state and may show the various components 1604 of the test (e.g., test card, swab, solution, and so forth). Each item in the test kit may be highlighted (for example, by dimming other elements, by changing the color of other elements (for example, displaying other elements in grayscale), by showing a glow around the item, by drawing a circle, rectangle, or other shape around the item, by pointing an arrow at the item, by animating the item (e.g., rotating and/or translating), and so forth). In some embodiments, the system may overlay the name of each element. After all items are shown, in some embodiments, the test box may fade out, leaving a prepared surface. In some embodiments, rather than showing all items in the test box, only some items may be shown. For example, the test kit may include additional material that is not needed for the testing session, such as printed instructions or a second set of test materials (e.g., a single box may include supplies for two tests).

Figure 17:
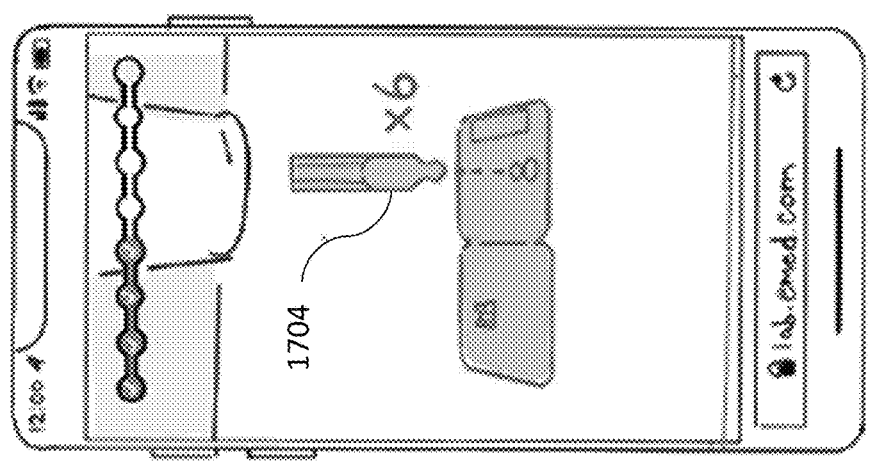
Figure 17:
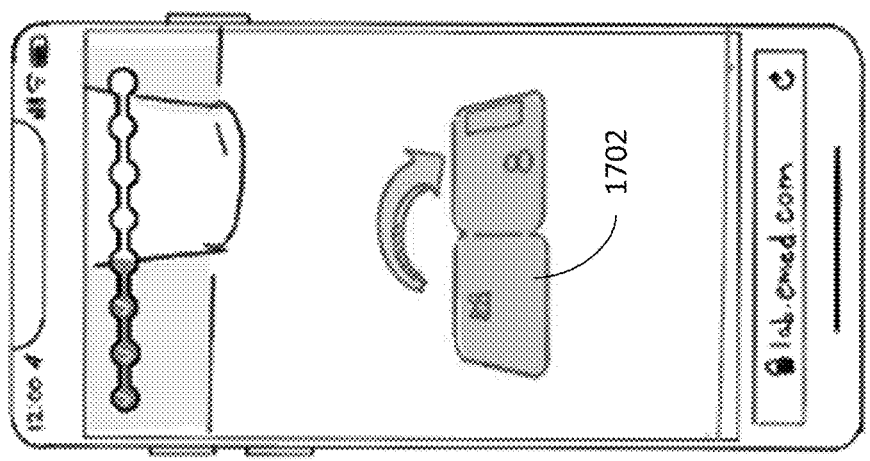

In FIG. 17, the system may show one or more key steps of the testing process and the virtual assistant or a pre-recorded message may narrate the process. In FIG. 17, the system shows an AR representation of opening a test card 1702 and applying solution 1704 to the test card 1702. Additional or different steps may be illustrated. For example, the system may explain steps such as swirling a sample collection device (e.g., a swab) in a solution or other steps as appropriate for the particular test the user is taking.

Figure 18:
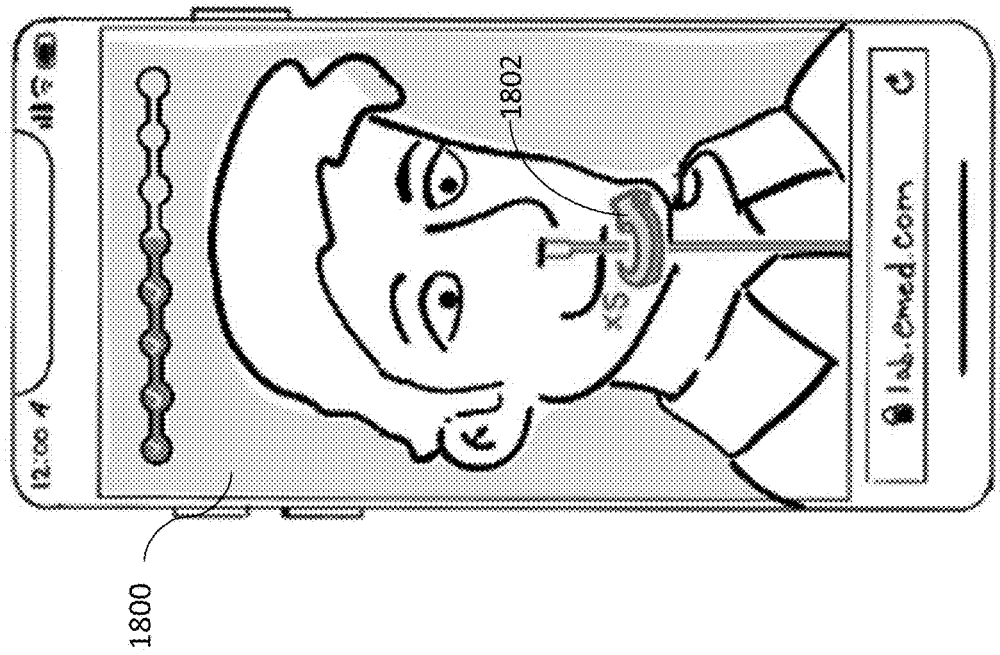

FIG. 18 depicts an example step in which a user-facing camera is used by the system to instruct the user. As depicted in FIG. 18, the system may use an image or video of the user 1800 and may overlay content 1802 that demonstrates how to perform sample collection, such as swabbing the user's nostrils, collecting a cheek swab, collecting a throat swab, and so forth.

Figure 19:
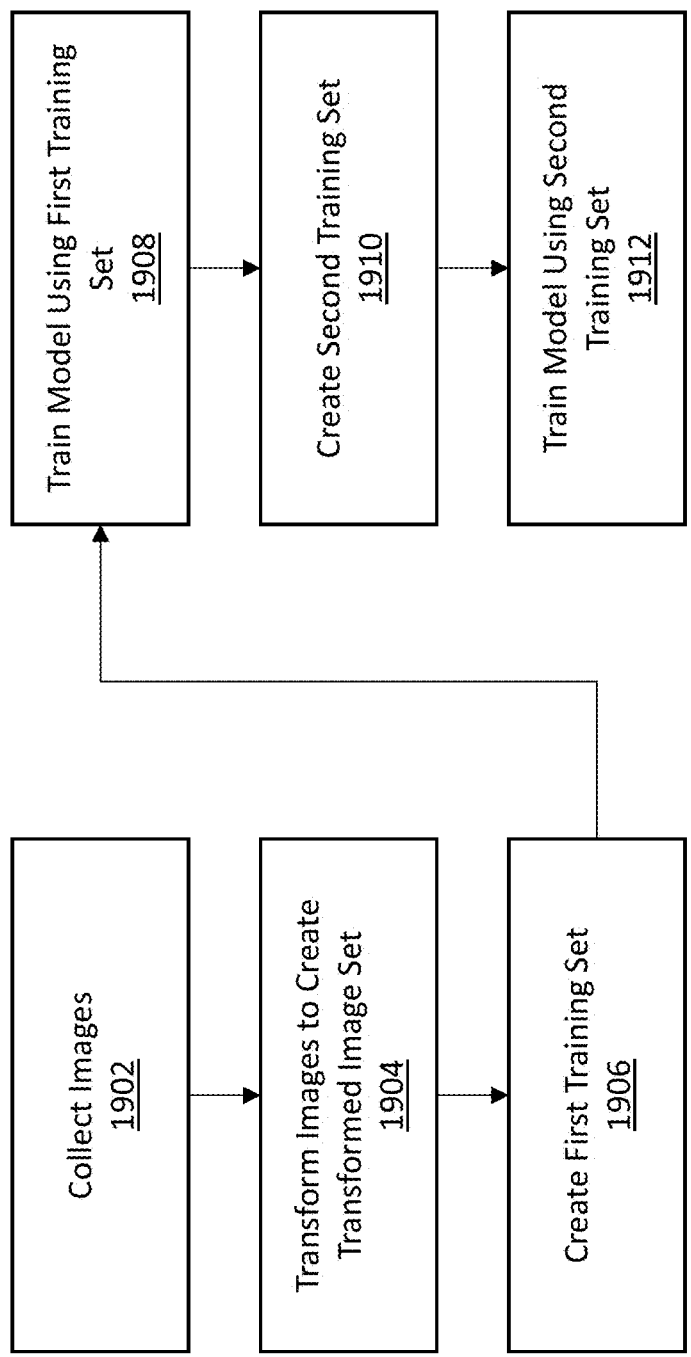
FIG. 19 is block diagram depicting model training according to some embodiments herein.

In some embodiments, the system may use machine learning and/or computer vision to detect the user's face and important features of the user's face (for example, the location of the user's nose in the case of a nasal swab or the user's mouth in the case of an oral swab). FIG. 19 is a block diagram that illustrates model training according to some embodiments. An artificial intelligence or machine learning model may be trained to detect facial features by, for example, at block 1902, collecting a set of facial images or videos from a database (e.g., captured video or images from prior testing sessions or from another source such as an available database of facial images), applying, at block 1904, one or more transformations to each image or video (for example, mirroring, rotating, smoothing, reducing or increasing contrast, reducing or increasing brightness, denoising, and so forth) to create a modified set of images or videos for training, creating, at block 1906 a first training set comprising the collected set of images or videos, the modified set of images or videos, and a set of non-pertinent images (e.g., images or videos of objects other than faces or where the face is obscured (e.g., by a mask) such that individual features such as nostrils or mouths are not visible), training the model at block 1908 using the first training set, creating a second training set containing the first training set and non-pertinent images that were misidentified during the first training at block 1910, and performing a second training of the model using the second training set at block 1912.

Figure 20:
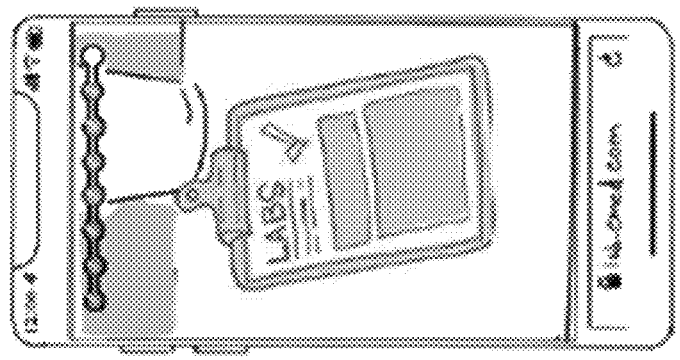
FIGS. 20-21 are example illustrations of some augmented reality tutorial steps according to some embodiments herein.
Figure 20:
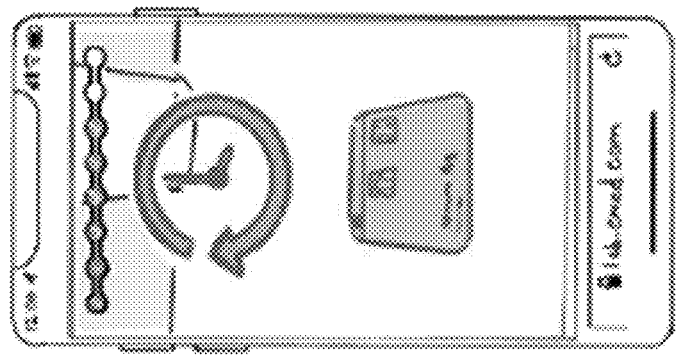
Figure 20:
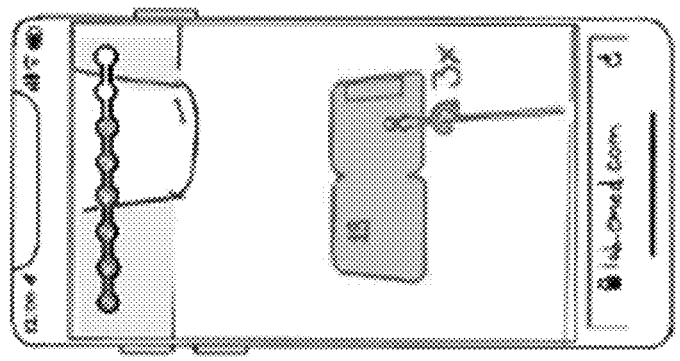

FIG. 20 shows an example of the system walking the user through one or more final steps in the testing process. For example, the system may show the user that they need to perform an action with a swab, may indicate that the user will need to wait for a period of time for test results to become available, may provide information about possible test results, and so forth.

Figure 21:
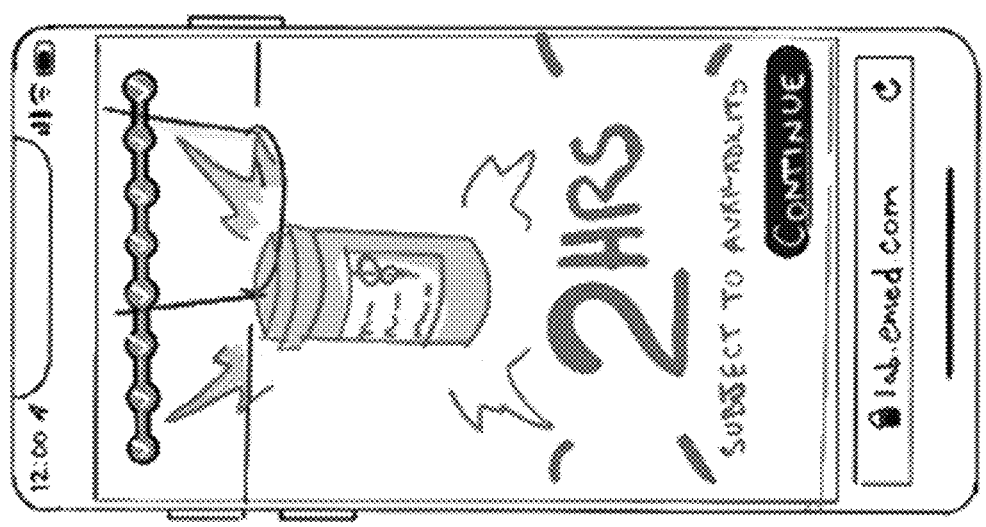

FIG. 21 depicts an example screen in which the system is configured to display a possible end result to the user. For example, if the test is for a condition for which a prescription treatment might be appropriate, the system may show that medication can be available within a short period of time. In some embodiments, the system may determine information such as the user's location, insurance coverage, and so forth. In some embodiments, the system may be configured to display different screens based on information such as the user's location, insurance coverage, and so forth, which may impact treatment delivery. For example, the system may be able to have prescriptions delivered to a user's home in some areas, while in other areas the user may need to visit a local pharmacy or receive treatment via mail. Similarly, the system may submit a request to an insurance provider to determine if a prescription will be covered, and if so, under what circumstances (for example, whether the patient can have the prescription sent via a delivery service or whether the patient needs to go to a pharmacy).

Proctor time reduction solutions exist on a gradient of technology complexity. For example, as described above, a preflight video may be relatively simple because it only requires that a system be capable of providing a video file or stream that the user's device can play. The AR preflight is more complex because virtual objects are overlaid onto the real world in a convincing manner. In some embodiments, because both low and high complexity solutions automate the same set of steps, it may be advantageous to implement the low complexity solution first. Individual steps can then be switched over to high complexity versions as they are developed and tested. For example, low complexity solutions may include providing instructions for users to follow.

In some embodiments, not all steps that can be automated may advantageously be automated. Low complexity steps may include, for example, capturing ID information, checking for a correct test box, device setup, unpacking and verifying components, scanning codes or results, and so forth. These may be implemented with limited use of computer vision or augmented reality. For example, steps may involve providing instructions to the user and/or capturing images or video for human review. Steps may also be implemented in a high complexity manner. For example, a system may use computer vision to automatically capture ID information, to check for a correct test box, to verify device setup, to verify components, to scan and interpret results, and so forth. High complexity solutions may also include features such as facial recognition to detect presence, audio quality checks, and so forth. In some embodiments, automating a step may save 5 seconds, 10 seconds, 15 seconds, 20 seconds, 30 seconds, 45 seconds, 60 seconds, 120 seconds, any number between these numbers, or even more. Greater proctor time reduction can be realized by implementing multiple automation steps.

In cases for which the testing queue is large, user experience and throughput can be improved by managing when the automated preflight starts. In one example, this can include determining the 5th percentile time it takes a user to complete the automated preflight (close to shortest), determine the position in queue a person needs to be, on average, for the above time to elapse before they are first in queue, and starting the automated preflight when the user reaches the above queue position. For example, the automated preflight can be started when the user is at queue position ten so that when they finish they are almost at queue position one. In some embodiments, if a user reaches queue position one before completing the preflight, that user can be temporarily skipped and reassigned to queue position one until the preflight is completed.

In some embodiments, the preflight portion can include an audio and/or video check.

FIGS. 22-32 illustrate example steps in a preflight portion that can be automated to decrease proctor time during proctored portions of a testing session. These steps are provided by way of example and are not intended to be interpreted in any limiting fashion. Different and/or additional steps may be automated.

Figure 22:
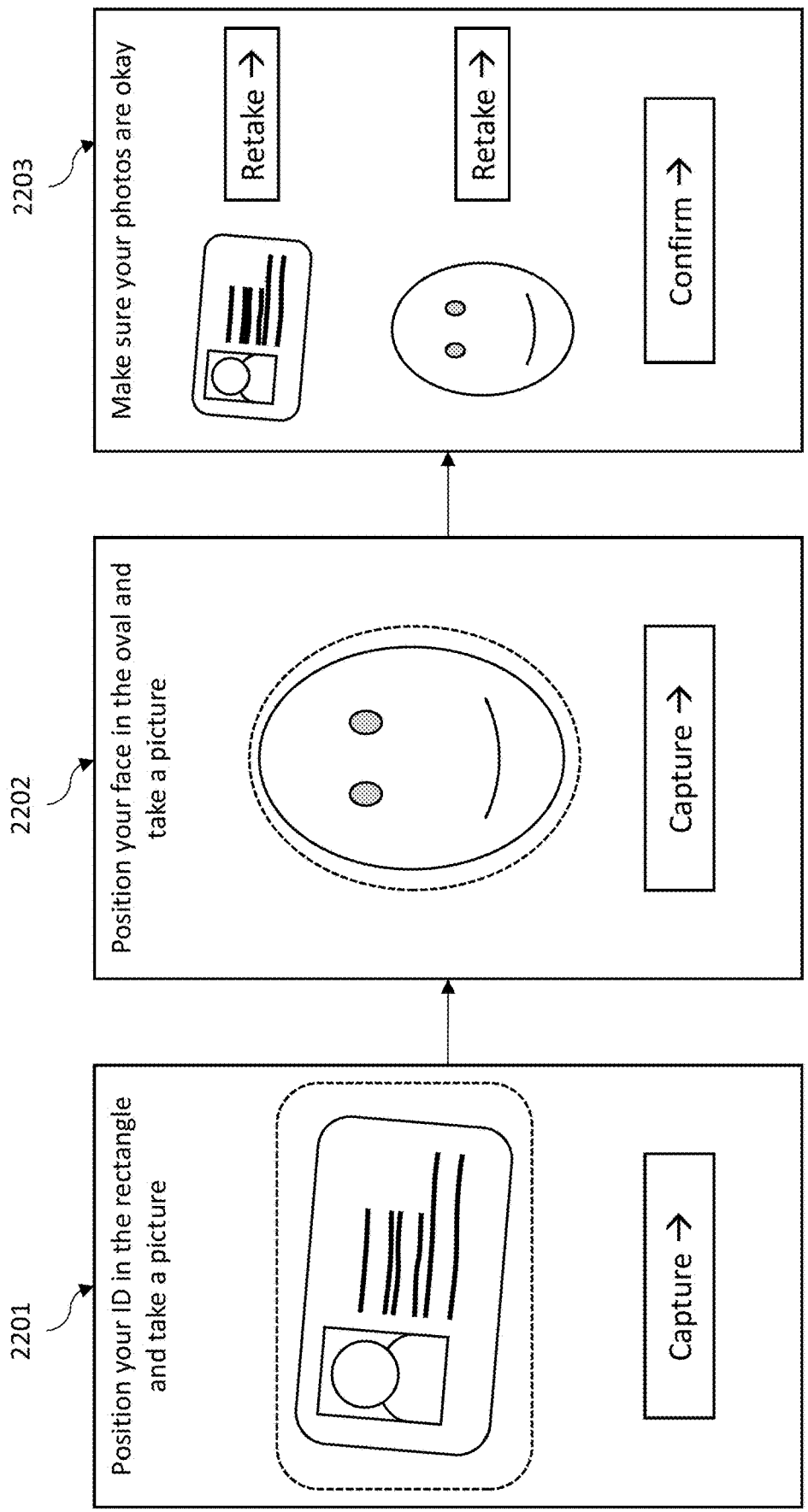
FIG. 22 illustrates an example interface for capturing identification information from a user according to some embodiments.

FIG. 22 illustrates capturing a user's identification and photograph according to some embodiments. At screen 2201, the user is asked to position their identification document (e.g., a driver's license or passport) within a frame and to capture a photo of their identification document. At screen 2202, the user is asked to position their face within a frame and to capture a photo. At screen 2203, the user shown the identification photo and the photo of the user's face and asked to confirm the photos. The screen 2203 may have buttons, links, and so forth that allow the user to recapture the identification document, the user's face, or both.

Figure 23:
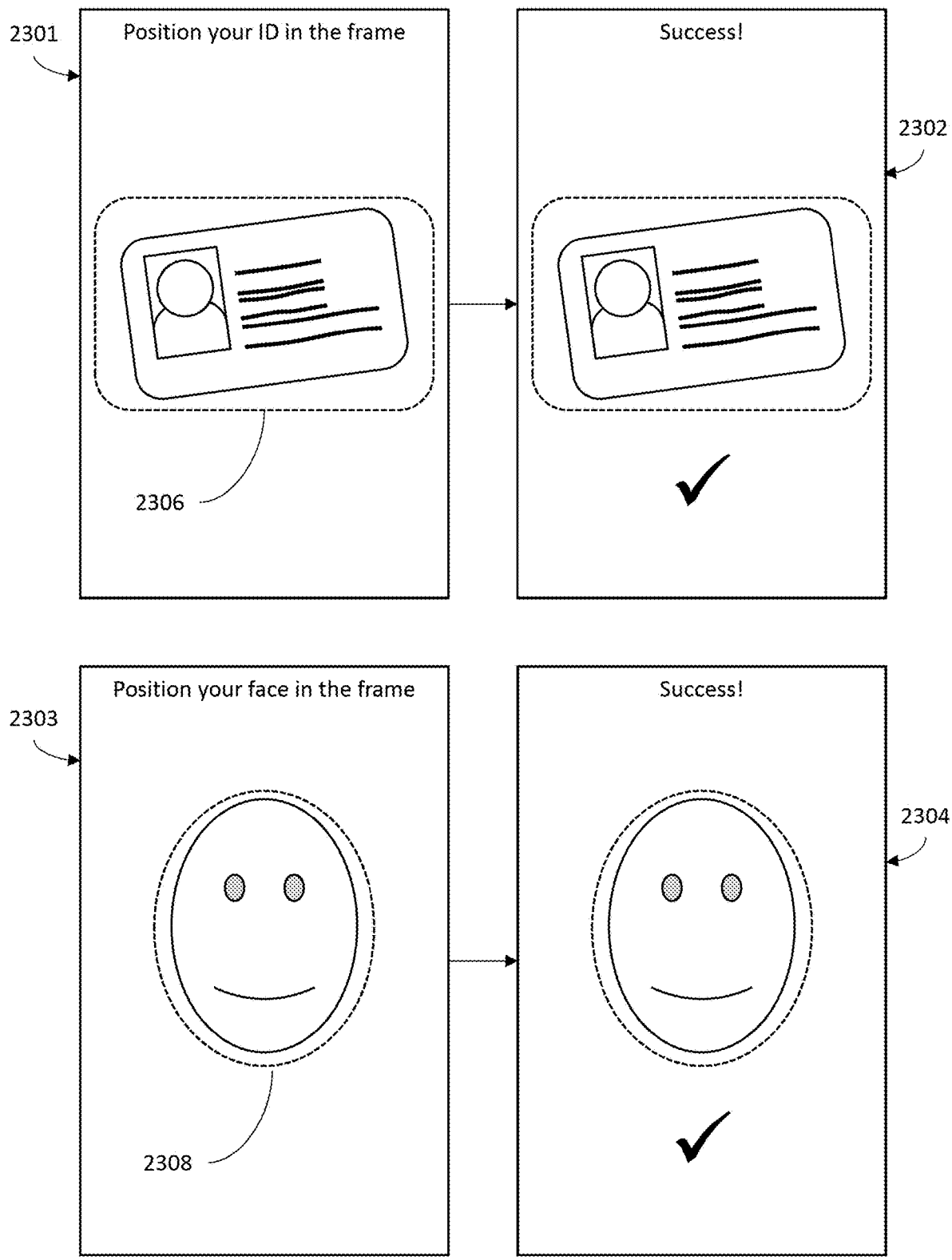
FIG. 23 illustrates an example interface for capturing identification information from a user according to some embodiments.

FIG. 23 illustrates capturing a user's identification and photograph in an automated process according to some embodiments. In some embodiments, rather than clicking or tapping a button to capture an image, an image may be automatically captured by a system after the system detects that an object of interest is within the frame of the camera on the user's device. At screen 2301, the user is asked to position their identification document (e.g., a driver's license or passport) within a frame 2306. The system may be configured with computer vision or artificial intelligence to detect when an identification document has been placed within the frame and may capture an image automatically after detecting that an identification document has been placed within the frame 2306. At screen 2302, the system may display an indication to the user that the identification document has been captured. Similarly, at screen 2303, the system may display a frame 2308 and ask the user to place their face within the frame. Upon detecting that a face is present in the frame 2308, the system may automatically capture an image and may display screen 2304 indicating to the user that an image has been captured. In some embodiments, the screens 2302 and/or 2304 may include an option for the user to retake an image.

Figure 24:
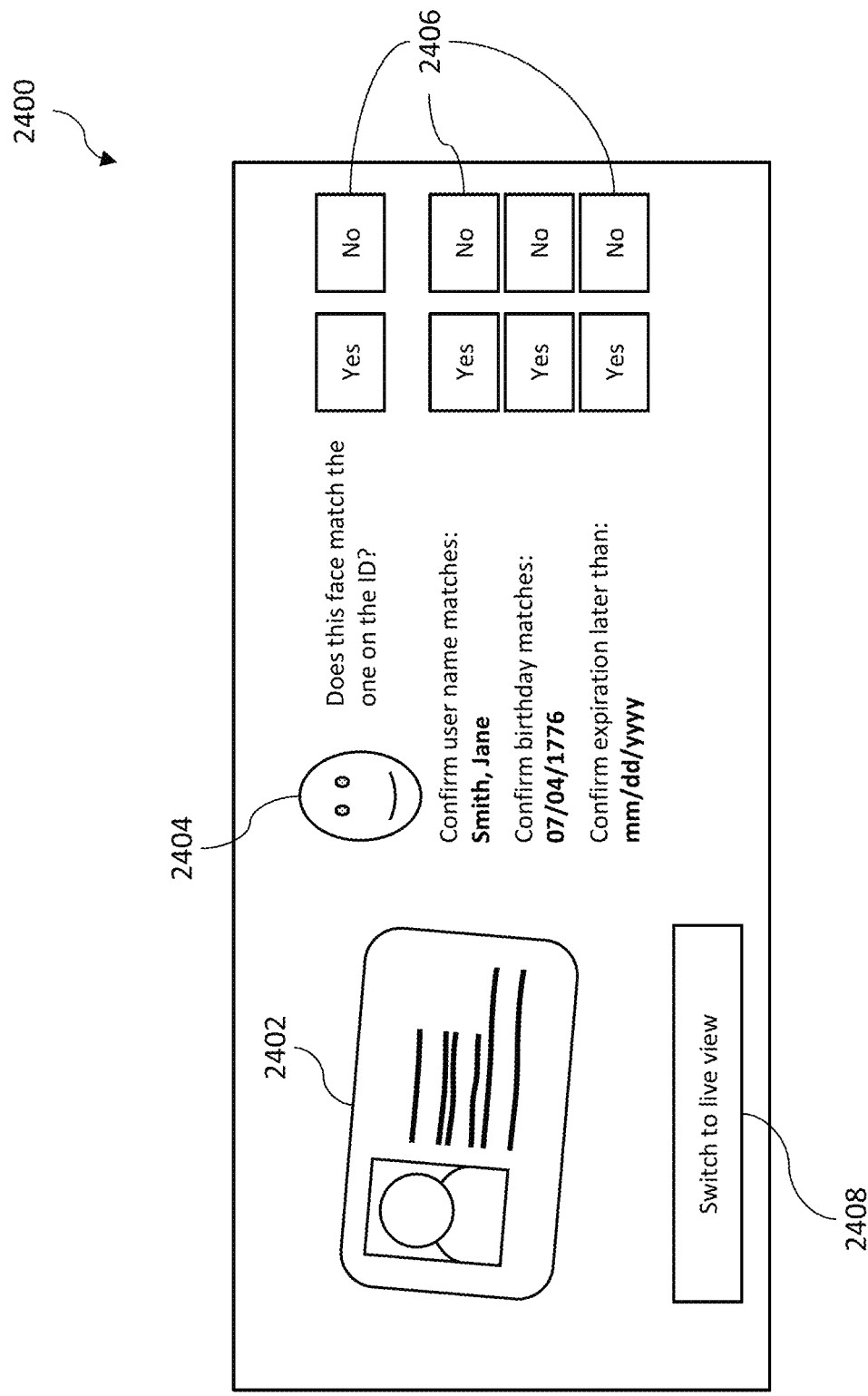
FIG. 24 illustrates an example interface for identity verification according to some embodiments.

In some embodiments, a test platform system may automatically assemble a page or view to present to a proctor for verification as shown in FIG. 24. The view 2400 may contain an image 2402 of the user's identification, a photo 2404 of the user, buttons 2406 that the proctor may use to indicate whether or not information has been verified, and a button 2408 that enables the proctor to switch to a live view of the user. In some embodiments, the proctor may be asked to confirm that the face matches in both images. The proctor may also be asked to confirm information on the identification document against information provided by the user during a registration process. In some embodiments, the proctor may be asked to confirm that the identification document is not expired or has expired within a threshold time period. In some embodiments, rather than or in addition to comparing information against registration information, a testing platform system may be configured to obtain data from other sources, such as driver databases, credit reporting agency databases, insurance provider databases, and so forth. In some embodiments, the system may extract information from the identification document and present it to the proctor for verification. In some embodiments, the system may convert the extracted information to a standardized format. For example, the system may arrange dates in a particular format (for example, "yyyy-mm-dd" or "mm/dd/ yyyy"), may convert names to a standardized format (for example, "<Last Name>, <First Name> <Middle Initial>"), and so forth.

Figure 25:
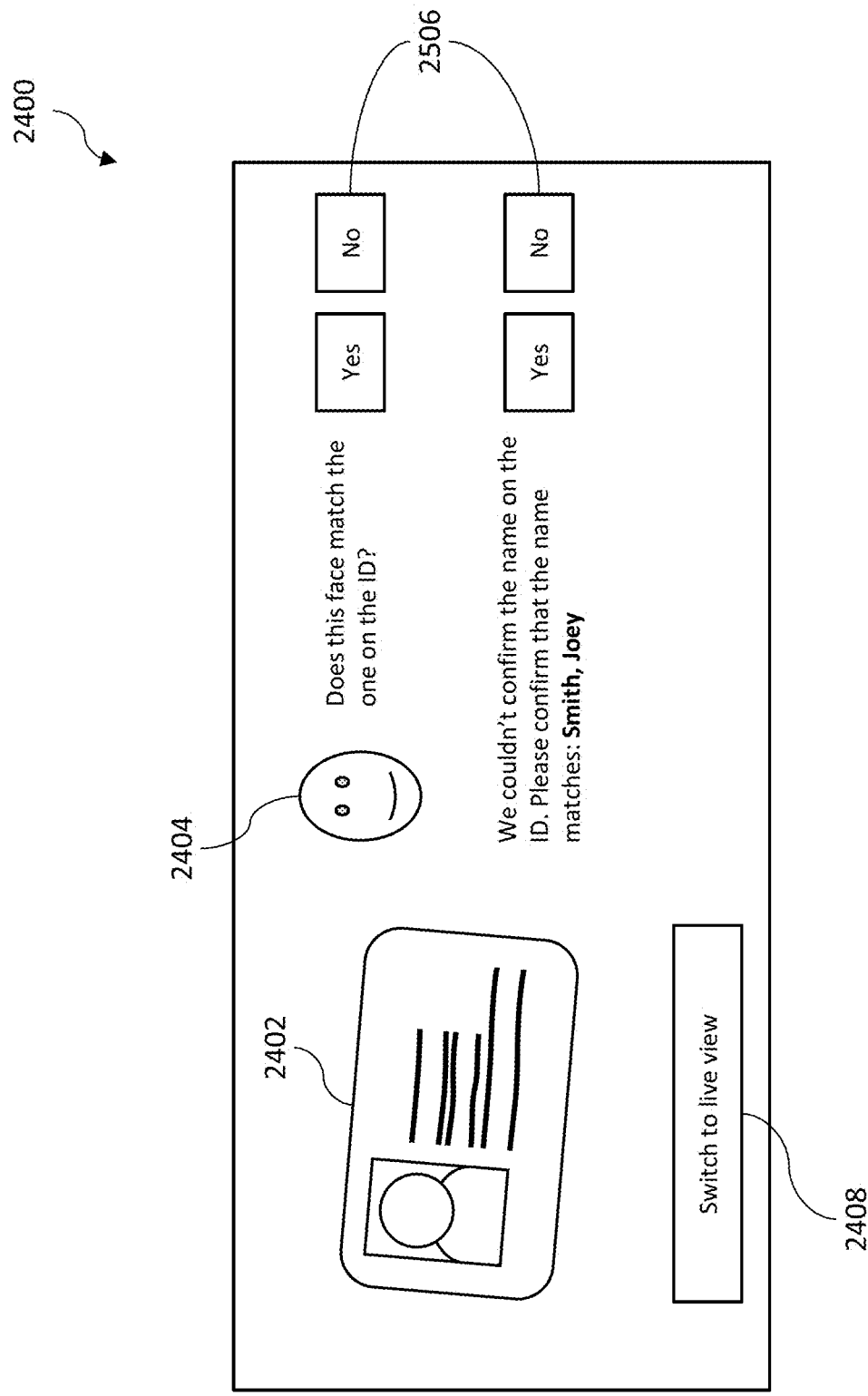
FIG. 25 illustrates an example interface for identity verification according to some embodiments.

In some embodiments, the system may be configured to automatically verify information. The system may compare the standardized information extracted from the identity document to reference information (e.g., registration information or information from a third party verification database). FIG. 25 depicts an example embodiment view that may be presented to a proctor. The view 2500 may contain an image 2402 of the user's identification, a photo 2404 of the user, buttons 2506 that the proctor may use to indicate whether or not information has been verified, and a button 1408 that enables the proctor to switch to a live view of the user. In FIG. 25, the proctor may only be shown information that was not automatically verified. For example, if a user enters a nickname or middle name as their first name during a registration process, the system may not be able to match the name on the identification document to the name entered during registration (for example, "Joey" instead of "Joseph"). In some embodiments, the system may not attempt to verify some information. For example, the system may try to verify text-based information but may not attempt to verify if the image of the user 2404 matches the person in the identification document image 2402. In some embodiments, the system may be equipped with artificial intelligence or machine learning functionality and may determine a likelihood that the person in the image and in the identification document is the same. In some embodiments, if the likelihood of a match is above a threshold amount, the system may not ask the proctor to verify the user's image.

Figure 26:
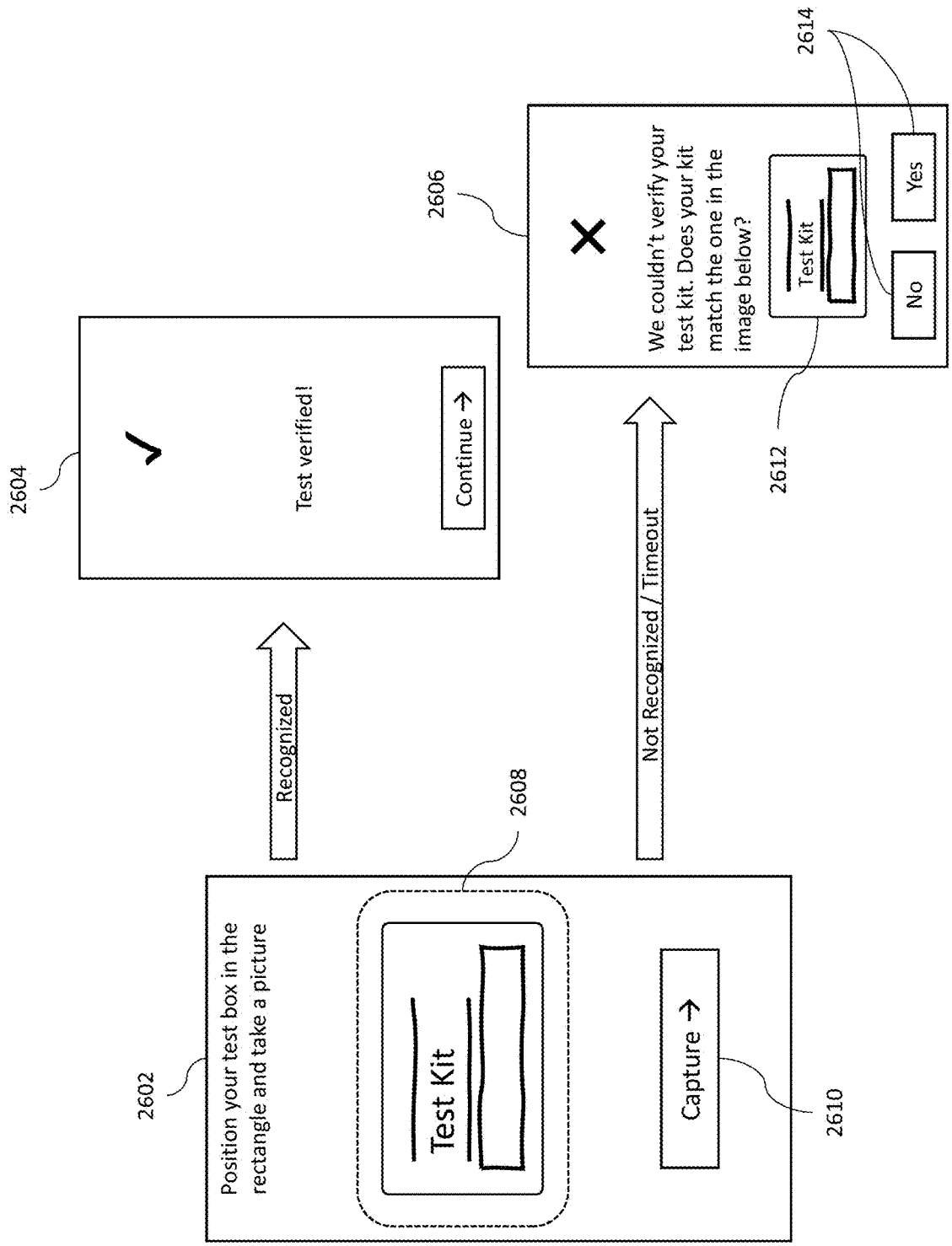
FIG. 26 illustrates an example embodiment of a test kit verification process and interface according to some embodiments.

FIG. 26 illustrates an example process for checking for a correct test box according to some embodiments. Screen 2602 includes a camera view 2608 and a capture button 2610. At screen 2602, the user is asked to take an image of the test box. In some embodiments, the user may capture an image by tapping the capture button 2610. Alternatively or additionally, the system may be configured to automatically capture an image upon detecting that a test kit (or similar object) has been placed within the camera view 2608. If the system recognizes the test kit as the right one for the test, the user may be shown screen 2604, which notifies the user that the kit has been verified. If the system does not recognize the kit in the image or the user doesn't capture an image after a period of time, the system may display screen 2606 to the user. Screen 2606 can include a reference image 2612 of a test kit and may ask the user if the kit they have matches the reference image 2612. If the user indicates that they do have the correct kit, the user may be prompted to again capture an image of the test kit (for example, by redirecting the user to screen 2602) or the user may be directed to support for further assistance. If the user indicates that they do not have the test kit depicted in the sample image, the user may be informed that the test procedure cannot move forward. In some embodiments, the user may be directed to an online store to purchase a test kit, provided information about nearby stores that sell test kits, and so forth. In some embodiments, the system may recognize the test kit using computer vision or artificial intelligence, for example by comparing the captured image to a reference image. In some embodiments, the system may be configured to look for a barcode, lot code, QR code, string of text, and so forth that may be used to identify the test kit.

Figure 27:
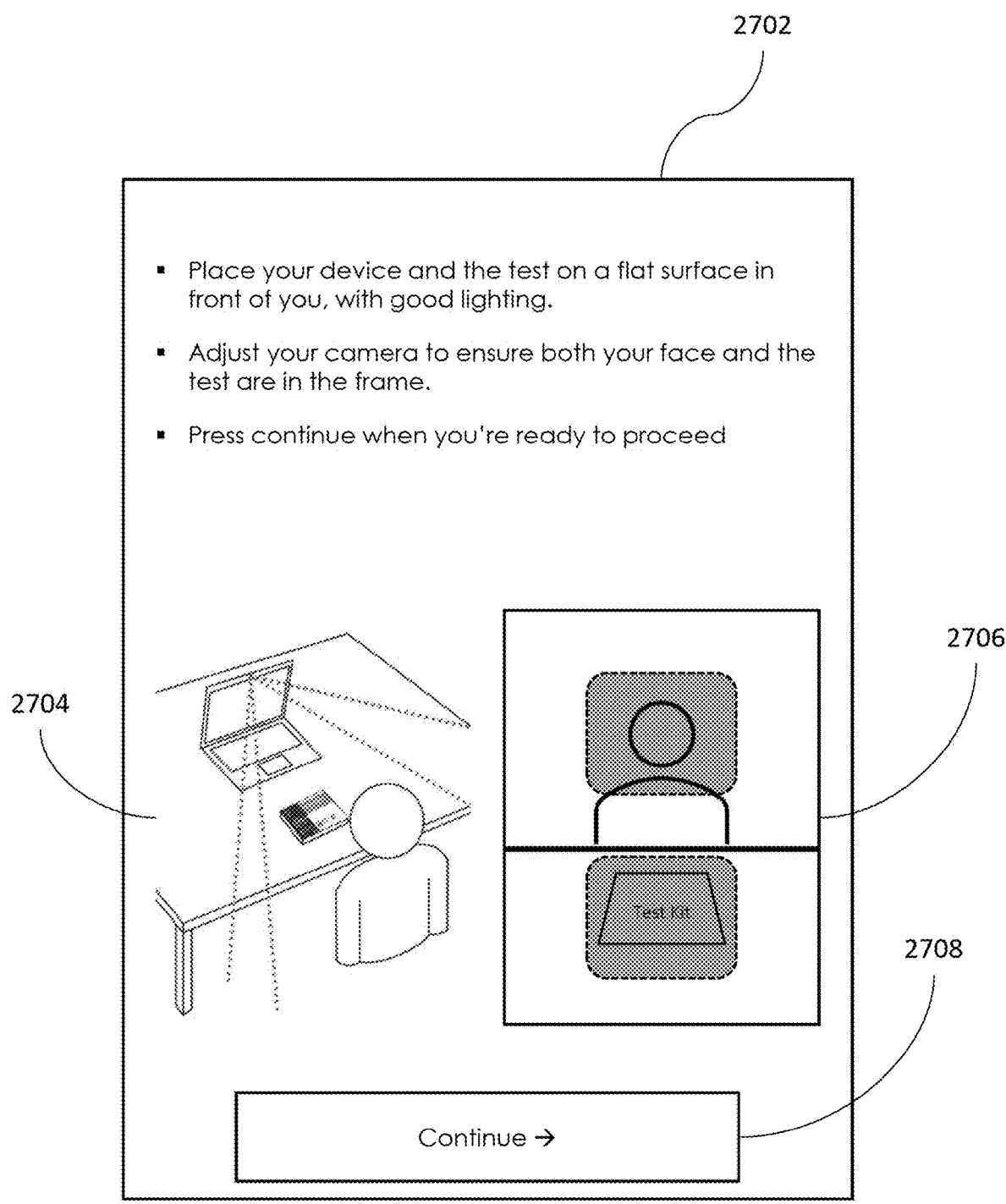
FIG. 27 illustrates an example user interface for testing setup according to some embodiments.

FIG. 27 is an illustration of testing setup according to some embodiments. In some embodiments, the system may aid the user in setting up the testing environment, for example to ensure that test kit materials and the user will be in view of the proctor. The system may display a screen 2702 to the user that contains instructions, a setup depiction 2704 (which may include, for example, images, animations, and so forth depicting correct device setup). The user may be presented with a live view 2706 of the user that has overlays indicating where the user should place their head and the test kit. In some embodiments, users may select between smartphone, tablet, laptop, or desktop configurations, or the system may automatically detect the type of device the user is using, for example by detecting the web browser, operating system, screen resolution, pixel density, user agent, and so forth. In some embodiments, the user may be instructed to remove materials from the test kit box and to place them in an indicated area. In some embodiments, this step may be entirely instructional to the user to help the user arrange their environment correctly for testing. In some embodiments, the system may extract information from the video feed, as discussed in more detail below. Once the user is ready to proceed, the user may click or tap the button 2708 to continue. In some embodiments, the setup step may include an audio check, for example to verify that the user's speakers and/or microphone are working.

Figure 28:
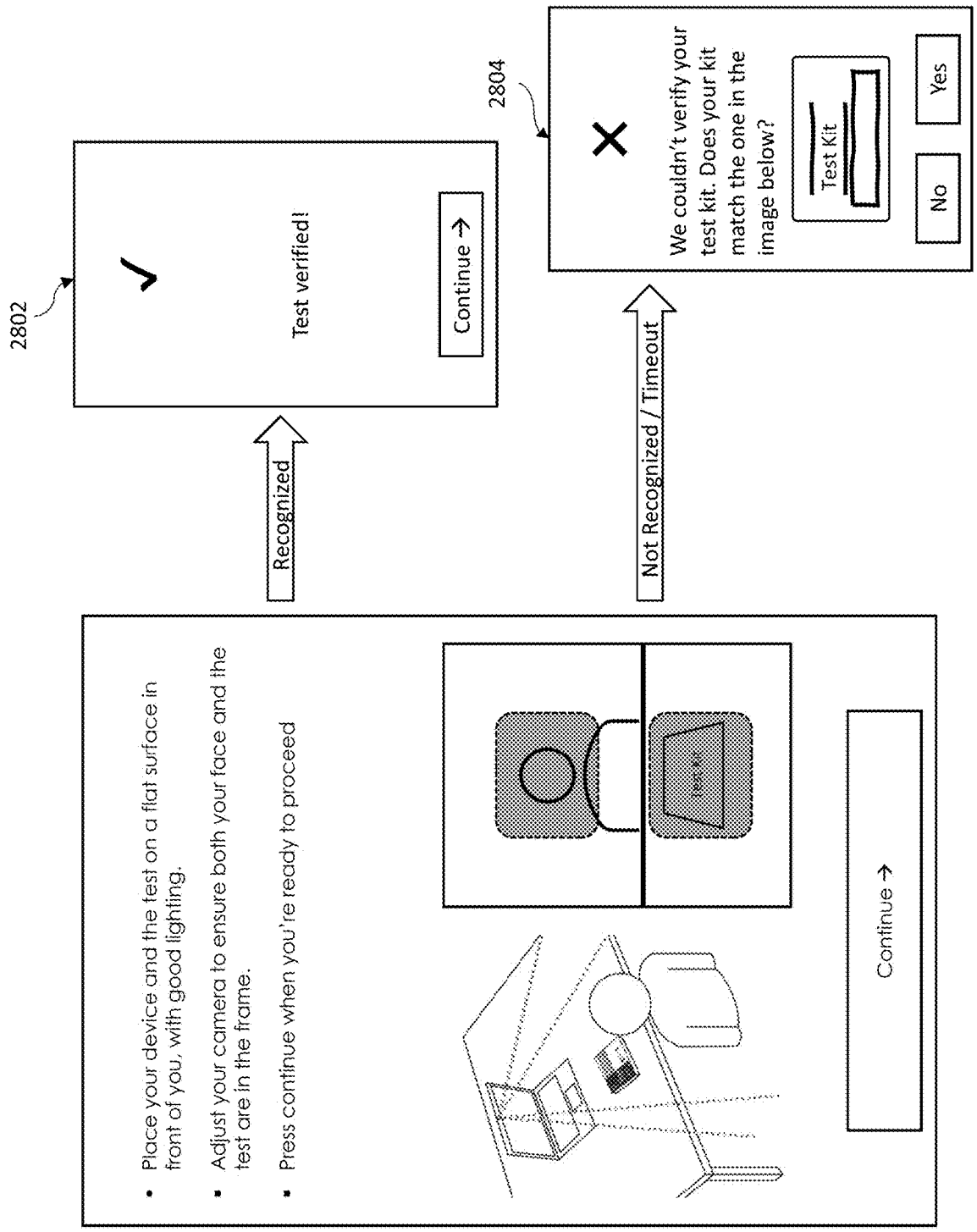
FIG. 28 illustrates an example embodiment of a testing setup and test kit verification process and interface according to some embodiments.

FIG. 28 is an illustration of testing setup according to some embodiments. As with FIG. 27, the user may be provided with example images, videos, or other instructions for setting up their testing environment, and the user may be presented with a live camera view with one or more overlays to help the user position items within the image frame. As depicted in FIG. 28, the system may capture one or more image frames and may use the captured image frames to make one or more determinations. For example, the system may extract from the video an image of the test kit and may attempt to verify that the user is using the correct test kit. In some embodiments, the system may use this approach as an alternative to having the user take a picture of the test kit as depicted in FIG. 26. If the system can verify the test kit, the user may be shown screen 2802. If the system cannot verify the test kit, the system may display screen 2804 to the user and ask them to confirm that they have the correct test kit. If the user indicates that they do have the correct test kit, the user may be redirected to support or may be asked to capture another image of their test kit, for example by following the procedure of FIG. 26, which may produce a better image of the test kit and may enable the system to verify the test kit without redirecting the user to support personnel.

Figure 29:
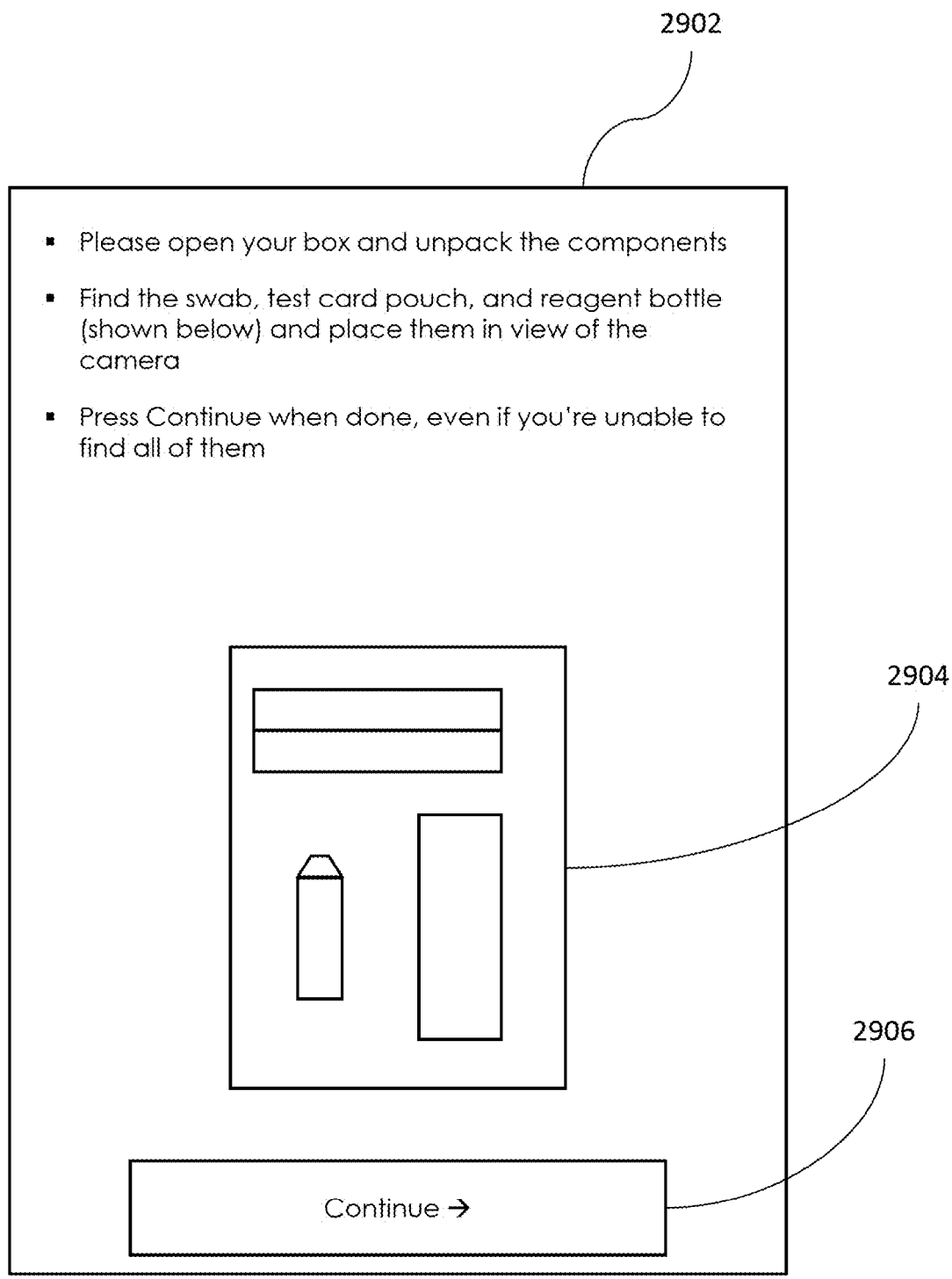
FIG. 29 illustrates an example interface for verifying test kit components according to some embodiments.
Figure 30:
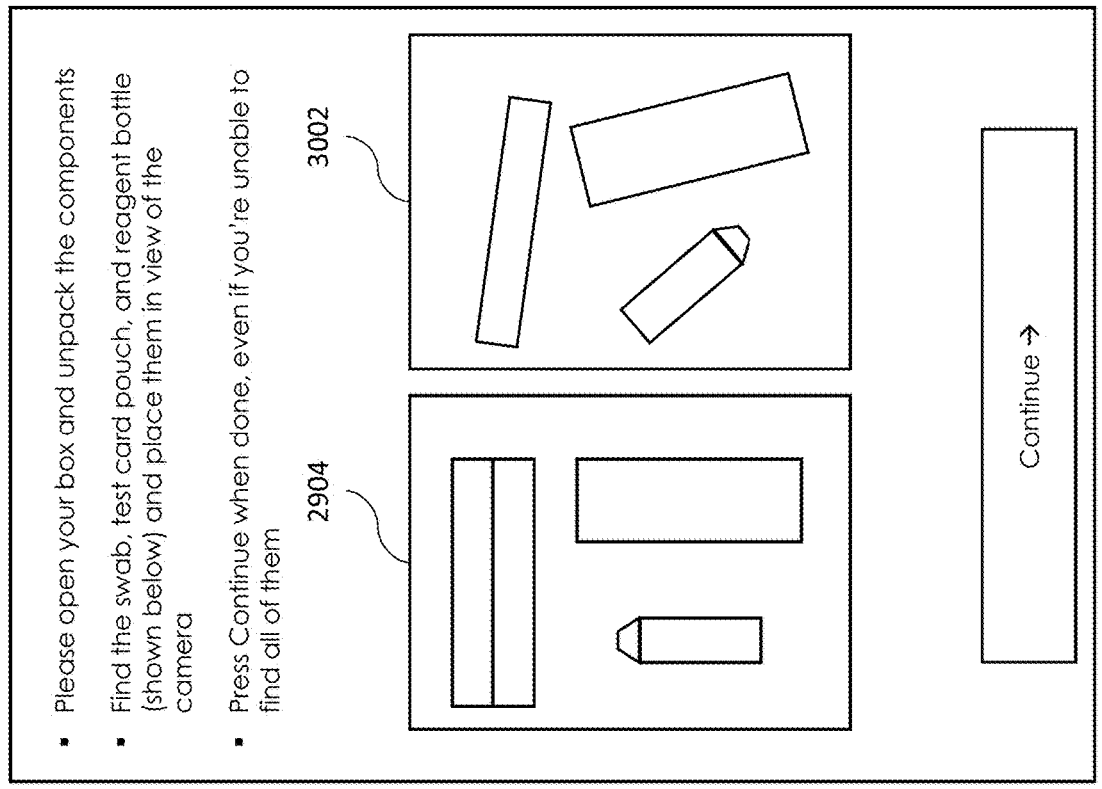
FIG. 30 illustrates an example interface and process for verifying test kit components according to some embodiments.

FIG. 29 is an example embodiment of a screen 2902 for instructing the user to unpack and verify test kit components. The user may be shown instructions, images, animations, and so forth and may be instructed to lay out the components in front of the camera. The screen 2902 may include an example image 2904 showing the contents of the test kit. The user may be instructed not to open some components, such as test swabs, test cards, and reagent bottles. The user may click or tap button 2906 to continue once the user is finished unpacking the test kit components. In some embodiments, the system may provide a live view and may attempt to verify the test kit components as shown in FIG. 30. The user may be shown a reference image 2904 and a live view 3002 from the user's camera. The system may verify components in the live view. In some embodiments, the system may detect that the expected components are present and proceed to the next step. In some embodiments, the user may proceed to the next step whether or not the components of the test kit could be verified. In some embodiments, the system may provide an indication to the proctor that the test kit components could not be automatically verified.

Figure 31B:
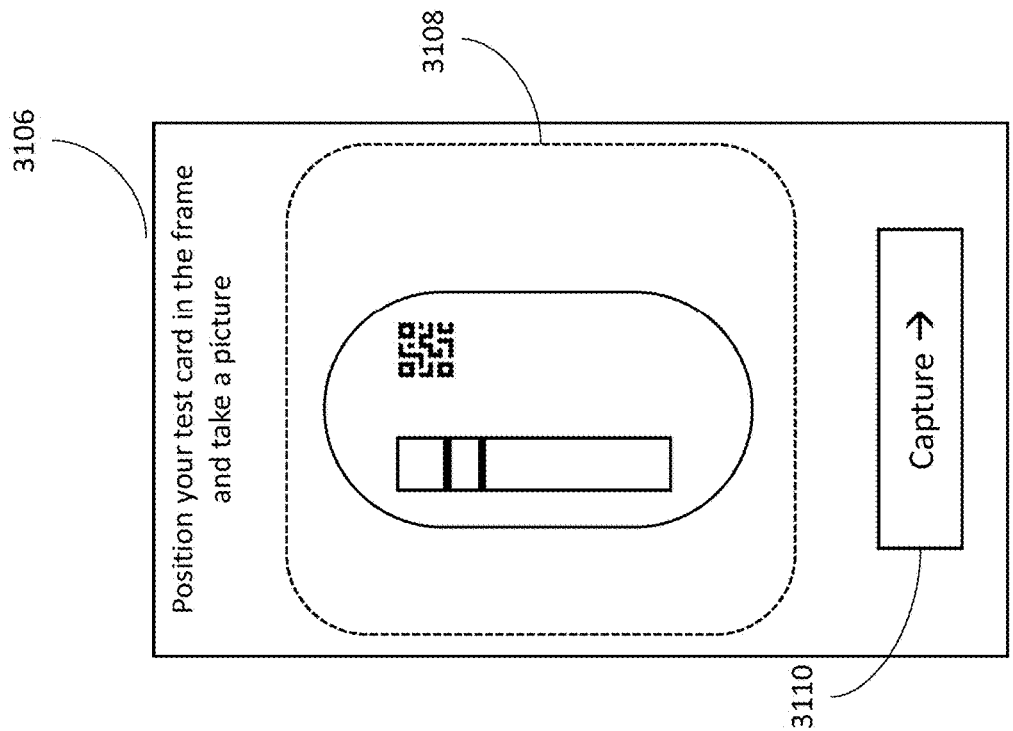
FIG. 31B illustrates an example user interface for resuming a testing session according to some embodiments.
Figure 31A:
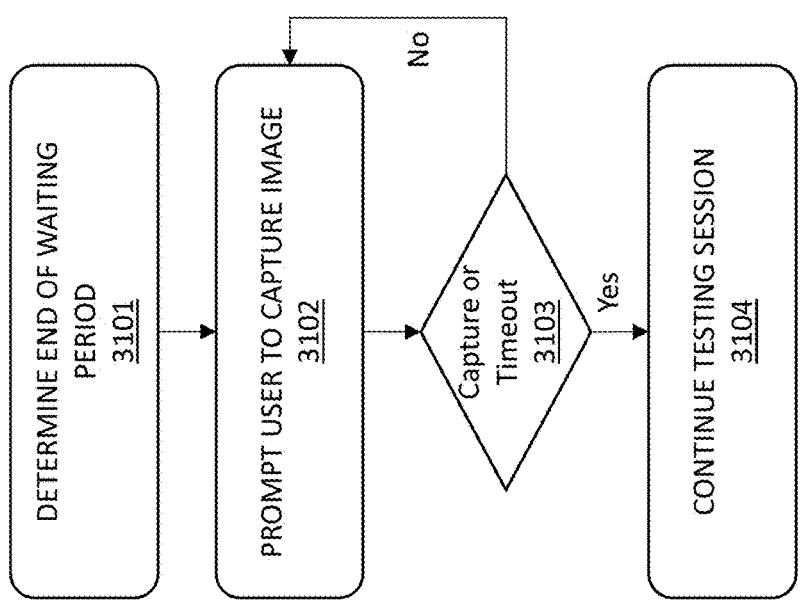
FIG. 31A illustrates an example process for resuming a testing session according to some embodiments.

In some cases, there may be a waiting period during the testing session. For example, a lateral flow test may take several minutes (e.g., ten or fifteen minutes) for results to become available. During this time, the proctor and user may do other things. For example, the proctor may attend to other users at different stages in the testing process. The system may be configured to prompt the user to resume the testing session after the waiting period. For example, the system may display an alert, play a sound, or otherwise notify the user that it is time to resume the testing session. As shown in FIG. 31A, the system may be configured to, at block 3101, determine the end of a waiting period. At block 3102, the system may prompt the user to capture an image (for example, an image of a test card or test strip). At decision point 3103, the system may determine if the user has captured an image or if a timeout threshold has been met. If the user has not captured an image and the timeout threshold has not been met, the system may continue prompting the user to capture an image. If the user has captured an image or the timeout threshold has been met, the system may continue the testing session at block 3104. FIG. 31B shows an example interface that may be presented to a user at block 3102. The screen 3106 may have a camera view 3108 and a capture button 3110. The screen may prompt the user to take a photo of the test card, test strip, or the like. In some embodiments, the test card or test strip may have a QR code, barcode, or other indicator that allows the system to identify the test card or strip, and the system may automatically continue after detecting the QR code, barcode, or other identifying indicator in the camera view 3108, or the system may ask the user to tap the capture button 3110 to continue. In some embodiments, the system may use computer vision and/or artificial intelligence to determine that the user has placed a test card or the like in the frame. In some embodiments, the prompt may time out after a threshold period of time and the testing procedure may continue with or without the image of the test card or test strip.

Figure 32:
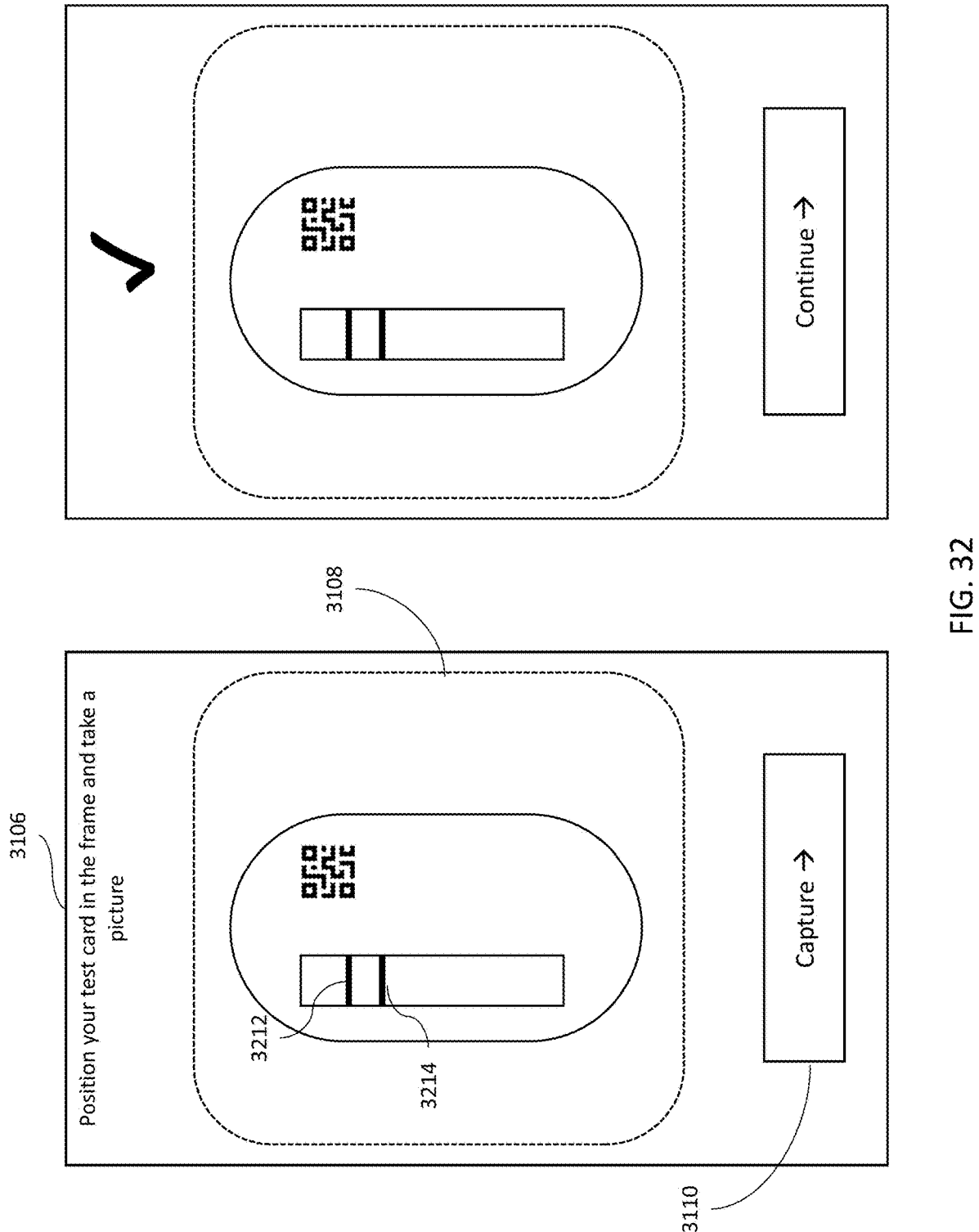
FIG. 32 illustrates an example user interface for capturing test results according to some embodiments.

In some embodiments, the image capture illustrated in FIGS. 31A and 31B may be used to capture test results. If an image was captured, the image may be provided by the system to the proctor for review. The proctor can review the image and interpret the results without having to ask the user to show the test card or test strip, saving time. If the image is blurry or otherwise unsuitable, the proctor can ask the user to show the test card or test strip. In some embodiments, the test results may be interpreted automatically (e.g., without a proctor). For example, the system may use computer vision or artificial intelligence to determine a test result based on the test card or strip. In some embodiments, the system may display an indication to the user that the test results have been captured, as illustrated in FIG. 32. The system may interpret results by, for example, interrogating a lateral flow test card image to determine if a control line 3212 is present. If the control line 3212 is not present, the system may automatically alert the user that the test is invalid. If the control line 3212 is present, the system may automatically alert the user of a positive or negative result based on the presence or absence of a test line 3214. In some embodiments, the system may not be able to determine a result, for example if the test card image is blurry, the lighting is poor, or the control and/or test lines are too faint. If the system cannot determine a result to at least a minimum level of confidence, the system may be configured to have a proctor review the result. In some embodiments, the proctor may ask the user to show their test card or strip again. In some embodiments, even if the system can automatically determine a result, the system may not display the result to the user. For example, for some types of tests or for some users, it may be advantageous for a proctor to provide the results to the user, for example if the user may benefit from additional explanation, if there is a need to discuss treatment or isolation, and so forth.

Computer Systems

FIG. 33 is a block diagram depicting an embodiment of a computer hardware system configured to run software for implementing one or more embodiments of the health testing and diagnostic systems, methods, and devices disclosed herein.

In some embodiments, the systems, processes, and methods described herein are implemented using a computing system, such as the one illustrated in FIG. 33. The example computer system 3302 is in communication with one or more computing systems 3320 and/or one or more data sources 3322 via one or more networks 3318. While FIG. 33 illustrates an embodiment of a computing system 3302, it is recognized that the functionality provided for in the components and modules of computer system 3302 may be combined into fewer components and modules, or further separated into additional components and modules.

The computer system 3302 can comprise an image processing module 3314 that carries out the functions, methods, acts, and/or processes described herein. The image processing module 3314 is executed on the computer system 3302 by a central processing unit 3306 discussed further below.

In general, the word "module," as used herein, refers to logic embodied in hardware or firmware or to a collection of software instructions, having entry and exit points. Modules are written in a programming language, such as JAVA, C or C++, Python or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 3302 includes one or more processing units (CPU) 3306, which may comprise a microprocessor. The computer system 3302 further includes a physical memory 3310, such as random-access memory (RAM) for temporary storage of information, a read only memory (ROM) for permanent storage of information, and a mass storage device 3304, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 3302 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 3302 includes one or more input/output (I/O) devices and interfaces 3312, such as a keyboard, mouse, touch pad, and printer. The I/O devices and interfaces 3312 can include one or more display devices, such as a monitor, that allows the visual presentation of data to a user. More particularly, a display device provides for the presentation of GUIs as application software data, and multi-media presentations, for example. The I/O devices and interfaces 3312 can also provide a communications interface to various external devices. The computer system 3302 may comprise one or more multi-media devices 3308, such as speakers, video cards, graphics accelerators, and microphones, for example.

The computer system 3302 may run on a variety of computing devices, such as a server, a Windows server, a Structure Query Language server, a Unix Server, a personal computer, a laptop computer, and so forth. In other embodiments, the computer system 3302 may run on a cluster computer system, a mainframe computer system and/or other computing system suitable for controlling and/or communicating with large databases, performing high volume transaction processing, and generating reports from large databases. The computing system 3302 is generally controlled and coordinated by an operating system software, such as z/OS, Windows, Linux, UNIX, BSD, SunOS, Solaris, macOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 3302 illustrated in FIG. 33 is coupled to a network 3318, such as a LAN, WAN, or the Internet via a communication link 3316 (wired, wireless, or a combination thereof). Network 3318 communicates with various computing devices and/or other electronic devices. Network 3318 is communicating with one or more computing systems 3320 and one or more data sources 3322. The image processing module 3314 may access or may be accessed by computing systems 3320 and/or data sources 3322 through a web-enabled user access point. Connections may be a direct physical connection, a virtual connection, and other connection type. The web-enabled user access point may comprise a browser module that uses text, graphics, audio, video, and other media to present data and to allow interaction with data via the network 3318.

Access to the image processing module 3314 of the computer system 3302 by computing systems 3320 and/or by data sources 3322 may be through a web-enabled user access point such as the computing systems' 3320 or data source's 3322 personal computer, cellular phone, smartphone, laptop, tablet computer, e-reader device, audio player, or another device capable of connecting to the network 3318. Such a device may have a browser module that is implemented as a module that uses text, graphics, audio, video, and other media to present data and to allow interaction with data via the network 3318.

The output module may be implemented as a combination of an all-points addressable display such as a cathode ray tube (CRT), a liquid crystal display (LCD), a plasma display, or other types and/or combinations of displays. The output module may be implemented to communicate with input devices 3312 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 3302 may comprise a physical or logical connection established between a remote microprocessor and a mainframe host computer for the express purpose of uploading, downloading, or viewing interactive data and databases on-line in real time. The remote microprocessor may be operated by an entity operating the computer system 3302, including the client server systems or the main server system, an/or may be operated by one or more of the data sources 3322 and/or one or more of the computing systems 3320. In some embodiments, terminal emulation software may be used on the microprocessor for participating in the micro-mainframe link.

In some embodiments, computing systems 3320 who are internal to an entity operating the computer system 3302 may access the image processing module 3314 internally as an application or process run by the CPU 3306.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 3302 may include one or more internal and/or external data sources (for example, data sources 3322). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 3302 may also access one or more databases 3322. The databases 3322 may be stored in a database or data repository. The computer system 3302 may access the one or more databases 3322 through a network 3318 or may directly access the database or data repository through I/O devices and interfaces 3312. The data repository storing the one or more databases 3322 may reside within the computer system 3302.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A computer-implemented method for a remote diagnostic testing platform, the computer-implemented method comprising:
   receiving, by a computing system, a video feed from a user device of a user engaging in an on-demand test session;
   analyzing, by the computing system, the video feed to automatically determine that a particular step in the on-demand test session has been reached by the user;
   based on detection of the particular step, storing, by the computing system, a plurality of subsequently-received image frames of the video feed to a first buffer;
   evaluating, by the computing system, the plurality of image frames stored in the first buffer against a set of criteria, wherein the evaluation comprises evaluating motion blur, a difference between a frame of the plurality of image frames and an adjacent image frame of the plurality of image frames, and a closeness of a camera exposure level to a predetermined exposure level;
   selecting, by the computing system, a subset of the image frames stored in the first buffer based at least in part on the evaluation;
   storing, by the computing system, the selected subset of image frames to a second buffer;
   processing, by the computing system, the subset of image frames stored in the second buffer to generate a composite image; and
   performing, by the computing system, one or more operations using the composite image.

2. The computer-implemented method of claim 1, further comprising detecting, by the computing system, that the particular step in the on-demand test session has ended.

3. The computer-implemented method of claim 1, wherein performing comprises presenting the composite image to a proctor.

4. The computer-implemented method of claim 1, wherein performing comprises creating or modifying a training data set, the training data set to be used for training a machine learning model.

5. The computer-implemented method of claim 1, wherein performing comprises:
   extracting, by the computing system, information from the composite image; and
   querying, by the computing system, a database using the extracted information.

6. The computer-implemented method of claim 1, wherein processing comprises:
   extracting, by the computing system, a region of interest from each image frame stored in the second buffer;
   using, by the computing system, template-matching to overlay image data extracted from the frames stored in the second buffer;
   processing, by the computing system, the overlaid image data to enhance the image; and
   combining, by the computing system, the processed overlaid image data to form a composite image.

7. The computer-implemented method of claim 6, wherein enhancing the image comprises any combination of one or more of suppressing noise, normalizing illumination, rejecting motion blur, enhancing resolution, rotating, keystone correcting, or increasing image size.

8. The computer-implemented method of claim 7, wherein normalizing illumination comprises:
   determining, by the computing system, a size of the region of interest in at least one dimension;
   accessing, by the computing system, a kernel for normalizing illumination levels in images;
   dynamically adjusting, by the computing system, a size of the kernel in at least one dimension based at least in part on the determined size of the region of interest; and
   applying, by the computing system, the adjusted kernel to one or more patches of the region of interest to normalize one or more levels of illumination within the region of interest.

9. The computer-implemented method of claim 6, further comprising:
   providing, to a proctor computing device, the composite image.

* * * * *